US011111043B2

(12) United States Patent
Coleman et al.

(10) Patent No.: US 11,111,043 B2
(45) Date of Patent: *Sep. 7, 2021

(54) SURGICAL KIT RECOVERY AND REUSE SYSTEM

(71) Applicant: CROSSROADS EXTREMITY SYSTEMS, LLC, Memphis, TN (US)

(72) Inventors: Robert Glen Coleman, Cordova, TN (US); Michael Chad Hollis, Collierville, TN (US); Vernon Raymond Hartdegen, Collierville, TN (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/285,141

(22) Filed: Feb. 25, 2019

(65) Prior Publication Data

US 2019/0185192 A1    Jun. 20, 2019

Related U.S. Application Data

(63) Continuation of application No. 14/869,870, filed on Sep. 29, 2015, now Pat. No. 10,252,829.

(Continued)

(51) Int. Cl.
*A61B 50/36* (2016.01)
*B65B 55/04* (2006.01)
(Continued)

(52) U.S. Cl.
CPC ............ *B65B 55/04* (2013.01); *A61B 17/80* (2013.01); *A61B 50/30* (2016.02); *A61B 50/33* (2016.02);
(Continued)

(58) Field of Classification Search
CPC ......... B65B 55/04; A61B 50/30; A61B 50/33; A61B 50/36; A61B 17/80; A61M 5/3205
(Continued)

(56) References Cited

U.S. PATENT DOCUMENTS 4,848,587 A * 7/1989 Nipp .................... A61M 5/003
                                                            206/571
5,374,813 A   12/1994 Shipp
(Continued)

FOREIGN PATENT DOCUMENTS

WO    WO2007005401    1/2007
WO    WO2007067105    6/2007
(Continued)

OTHER PUBLICATIONS

Biomet. ePAK™ Single-Use Delivery System featuring DVR® Crosslock. Economic Buyer Brochure. 2013.
(Continued)

*Primary Examiner* — King M Chu
(74) *Attorney, Agent, or Firm* — David Meibos; Maywood IP Law

(57) ABSTRACT

A terminally sterilized medical procedure kit includes a recovered item and a new item packaged together as a single stock keeping unit. A method for processing at least a portion of a first medical procedure kit includes the steps of receiving a recoverable item of the first kit, performing a processing operation on the recoverable item, providing a new item, combining the recoverable item and the new item in a second kit, and terminally sterilizing the second kit. A method for recovering at least a portion of a terminally sterilized medical procedure kit includes the steps of purchasing a recoverable item of the first kit from an owner and receiving the recoverable item by the purchaser.

6 Claims, 14 Drawing Sheets

Related U.S. Application Data

(60) Provisional application No. 62/106,713, filed on Jan. 22, 2015.

(51) Int. Cl.

| | | |
|---|---|---|
| *A61B 17/80* | (2006.01) | |
| *A61L 2/04* | (2006.01) | |
| *A61F 2/00* | (2006.01) | |
| *B65B 55/12* | (2006.01) | |
| *G06Q 90/00* | (2006.01) | |
| *A61B 50/30* | (2016.01) | |
| *A61B 50/33* | (2016.01) | |
| *A61B 90/70* | (2016.01) | |

(52) U.S. Cl.
CPC ............ *A61B 50/36* (2016.02); *A61F 2/0095* (2013.01); *A61L 2/04* (2013.01); *B65B 55/12* (2013.01); *G06Q 90/00* (2013.01); *A61B 90/70* (2016.02); *A61B 2050/3008* (2016.02); *A61L 2202/21* (2013.01); *A61L 2202/24* (2013.01)

(58) Field of Classification Search
USPC ........................................ 206/571, 572, 570
See application file for complete search history.

(56) References Cited

U.S. PATENT DOCUMENTS

| | | |
|---|---|---|
| 5,676,255 A | 10/1997 | Flowers |
| 5,988,171 A | 11/1999 | Sohn |
| 6,206,858 B1 | 3/2001 | Kempen |
| 6,640,976 B1 | 11/2003 | Franks-Farah |
| 6,808,255 B1 | 10/2004 | Haines |
| 7,562,025 B2 | 7/2009 | Mallett |
| 7,591,380 B2 | 9/2009 | Bennett |
| 7,677,395 B2 | 3/2010 | Bennett |
| 7,934,602 B2 | 5/2011 | Bennett |
| 7,984,810 B2 | 7/2011 | Bennett |
| 8,061,528 B2 | 11/2011 | Bennett |
| 8,522,979 B2 | 9/2013 | Bennett |
| 9,375,303 B1 | 6/2016 | Cook |
| 10,252,829 B2 | 4/2019 | Coleman |
| 2002/0065744 A1 | 5/2002 | Collins |
| 2003/0040950 A1 | 2/2003 | Iwasaka |
| 2003/0055753 A1 | 3/2003 | Dellar |
| 2004/0249671 A1 | 12/2004 | Noguchi |
| 2005/0125248 A1 | 6/2005 | Butterworth |
| 2005/0226682 A1 | 10/2005 | Chersky |
| 2006/0059018 A1 | 3/2006 | Shiobara |
| 2006/0136249 A1 | 6/2006 | Kagan |
| 2006/0190342 A1 | 8/2006 | Dendl |
| 2007/0083286 A1 | 4/2007 | Kobayashi |
| 2007/0094303 A1 | 4/2007 | Zwingenberger |
| 2008/0254471 A1 | 10/2008 | Bordano |
| 2010/0070389 A1 | 3/2010 | Farabola |
| 2010/0076344 A1 | 3/2010 | Kecman |
| 2011/0156903 A1 | 6/2011 | Henniges |
| 2011/0238977 A1 | 9/2011 | Talbert |
| 2011/0270708 A1 | 11/2011 | Walden |
| 2012/0116380 A1 | 5/2012 | Madan |
| 2012/0253357 A1 | 10/2012 | Mandpe |
| 2012/0267272 A1 | 10/2012 | Agrawal |
| 2012/0303004 A1 | 11/2012 | Uthgenannt |
| 2013/0213843 A1 | 8/2013 | Knight |
| 2013/0226183 A1 | 8/2013 | Xie |
| 2013/0310829 A1 | 11/2013 | Cohen |
| 2014/0032232 A1 | 1/2014 | Brown |
| 2014/0052135 A1 | 2/2014 | Aman |
| 2014/0082910 A1 | 3/2014 | Sullivan |
| 2014/0231302 A1 | 8/2014 | Goyal |
| 2014/0276947 A1 | 9/2014 | Lambrecht |
| 2014/0336778 A1 | 11/2014 | Termanini |
| 2014/0343553 A1 | 11/2014 | Ford |
| 2014/0358130 A1* | 12/2014 | Gardner ............... A61B 50/33 606/1 |
| 2015/0083627 A1 | 3/2015 | Gorman |
| 2015/0119652 A1 | 4/2015 | Hyde |
| 2015/0148791 A1 | 5/2015 | Birdsall |
| 2015/0196363 A1 | 7/2015 | Aman |
| 2016/0059980 A1 | 3/2016 | Nemec |
| 2016/0214753 A1 | 7/2016 | Coleman |
| 2016/0217542 A1 | 7/2016 | Coleman |

FOREIGN PATENT DOCUMENTS

| | | |
|---|---|---|
| WO | WO2007143087 | 12/2007 |
| WO | WO2010004330 | 1/2010 |
| WO | WO2011063231 | 5/2011 |
| WO | WO2015017677 | 2/2015 |
| WO | WO2016118196 | 7/2016 |

OTHER PUBLICATIONS

Biomet. ePAK™ Single-Use Delivery System featuring DVR® Crosslock. Surgical Team Brochure. 2013.

Flower Orthopedics. Home page. http://www.flowerortho.com/home.html. Viewed Dec. 28, 2015.

Flower Orthopedics. The FlowerCube™ Single-Use, Surgery-Specific, Bone-Fixation Applications. 2014.

Stryker. Stryker Sustainability Solutions page. http://sustainability.stryker.com/about. Viewed Dec. 28, 2015.

* cited by examiner

SURGICAL KIT RECOVERY AND REUSE SYSTEM

CROSS-REFERENCE TO RELATED APPLICATIONS

The present application is a continuation application of U.S. patent application Ser. No. 14/869,870 filed on Sep. 29, 2015, entitled "Surgical Kit Recovery and Reuse System", which claims the benefit of U.S. Provisional Application Ser. No. 62/106,713, entitled "Surgical Kit Recovery and Reuse System", which was filed on Jan. 22, 2015. The foregoing are incorporated herein by reference as though set forth in their entirety.

TECHNICAL FIELD

The disclosed technology is in the field of medical technology. More particularly, the disclosed technology is in the field of kitting and/or packaging of medical device systems. The disclosed technology includes a system or process for providing single procedure kits to an end user, providing a means of recovering certain components of the kit for reuse, and combining those recovered or reprocessed components with new device(s), implant(s), and or components to be kitted together in a single sterile kit.

BACKGROUND

In the field of medical devices there is a move towards providing sterile packaged, single use items. Providing sterile, single use, disposable kits may tend to provide better sterility assurance and operational efficiencies, such as reduced cost to process kits prior to surgery or reduced chance of surgical delays due to missing components. However, single use, disposable kits may also increase waste due to additional packaging materials required for sterilization and due to discarding of the "disposable" medical instruments or components that were contained in the kit, whether each of the disposable items was actually used or not. In current sterile kits, components of the kits are typically manufactured or produced in such a manner that makes them unsuitable for reprocessing or reuse. For example, components may be flimsy, difficult to clean or sterilize, or subject to degradation as a result of use, cleaning, or sterilization. Also, current sterile kits do not provide a mechanism, process, or system for reusing components that were not consumed during the initial use of the sterile kit. Said another way, the components of current sterile kits are typically intended to be disposed of after the surgery is completed, whether each component is actually used in surgery or not. In addition, current sterile kits do not recombine the non-consumed kit components from a previous kit for continued service or use with new devices in a sterile kit. More precisely, current sterile kits do not recombine the non-consumed kit components with new implants.

SUMMARY

The disclosed technology provides apparatus, systems, methods, and processes for preparing, assembling, or building a sterile single procedure kit that includes a recovered component and a new component. The recovered component may be recovered from a previous sterile single procedure kit after that kit is used in a medical procedure.

The technology disclosed herein may provide improved sterility assurance and greater efficiencies compared to reusable instruments or surgical kits that require the end user to sterilize each kit prior to surgery while reducing waste and improving reliability of sterile kits. The technology disclosed herein may provide a process or system that allows components of sterile kits to be manufactured or produced in a way that may provide a robust design for the intended use and would allow the components to have a service life that may exceed that of typical sterile kit components. The current technology may also provide component designs that may be reprocessed and reused in sterile kits. In addition, the disclosed technology may also provide a system or container that would allow storage and transport of the non-consumed devices as the non-consumed devices are recovered. The disclosed technology may also provide a means for transfer of ownership of the devices. The disclosed technology may also provide a means, process, or system for reusing components that were not consumed during the initial use of the sterile kit. This may include the ability to recombine the non-consumed kit components with new devices for continued service or use, the ability to reprocess or refurbish the non-consumed kit components, or the ability to recycle the non-consumed kit components as sub-assemblies, individual parts, or raw materials. The steps for reprocessing of components may include placement of the devices in a container for shipment, repurchasing, cleaning, sterilizing, refurbishing, repackaging, relabeling, re-sterilizing, and re-selling of the components.

The system may include instruments, implants, packaging, and or other components and/or a container. The system may include implants of varying sorts and quantities, instruments of varying sorts and quantities, packaging of varying sorts and quantities, and other single use, consumable devices of various sorts and quantities. One aspect of the system may include the sterile kit, the container, and the process of recombining non-consumable device(s) with a new consumable device(s) in a new kit having a shared or common sterile barrier, or individual sterile barriers and a shared or common carton or box.

The process may include the steps of reprocessing and or recovering certain contents of the kit that are not consumed at the time of use. The contents that may be recovered may include surgical tools/instruments, packaging, implants or the like that were not consumed during the initial use of the surgical kit. The process may include a process, step, or subroutine for acquiring the non-consumed kit components from the end user or hospital. The non-consumed or reusable components or devices may be stored and or transported in a container specifically for this purpose.

An aspect of the technology is a method for processing at least a portion of a first kit, wherein the first kit is used in a medical procedure and includes a first recoverable item. The method includes the steps of: after the first kit is used in the medical procedure, receiving the first recoverable item for processing; performing a processing operation on the first recoverable item, wherein the processing operation is selected from the group consisting of receiving, cleaning, disinfecting, sterilizing, inspecting, testing, marking, refurbishing, recycling, and stocking; providing a new item; after performing the processing operation on the first recoverable item, combining the first recoverable item and the new item in a second kit; and terminally sterilizing the second kit.

Various embodiments of this aspect of the technology may include one or more of the following. After the first kit is used in the medical procedure, receiving a second recoverable item of the first kit for processing; and performing a processing operation on the second recoverable item, wherein the processing operation on the second recoverable item is selected from the group consisting of receiving, cleaning, disinfecting, sterilizing, inspecting, testing, marking, refurbishing, disassembling, recycling, stocking, and discarding. After performing the processing operations on the first and second recoverable items, combining the first and second recoverable items and the new item in the second kit. The processing operation on the second recoverable item may differ from the processing operation on the first recoverable item. After the first kit is used in the medical procedure, receiving a first reusable item of the first kit for processing; and performing a processing operation on the first reusable item, wherein the processing operation on the first reusable item is selected from the group consisting of receiving, cleaning, disinfecting, sterilizing, inspecting, testing, marking, refurbishing, recycling, and stocking. After performing the processing operations on the first recoverable item and the first reusable item, combining the first recoverable item, the first reusable item, and the new item in the second kit. The processing operation on the first reusable item may differ from the processing operation on the first recoverable item. The first recoverable item may consist of materials that are impervious to repeated terminal sterilization. The first recoverable item may consist of metal. The first recoverable item may be a medical instrument. The new item may be a medical implant. After the first kit is used in the medical procedure, transferring ownership of the first recoverable item to a recipient. Transferring ownership of the first recoverable item may include the recipient buying the first recoverable item. Providing a container to receive the first recoverable item after the first kit is used in the medical procedure. Removing the first recoverable item from the container before performing the processing operation on the first recoverable item. The first kit may include the container. The container may be a package that contained the first recoverable item. Performing a processing operation on the first recoverable item may include: performing a first processing operation on the first recoverable item, wherein the first processing operation is selected from the group consisting of cleaning, disinfecting, and sterilizing; performing a second processing operation on the first recoverable item, wherein the second processing operation is selected from the group consisting of refurbishing and recycling; and performing a third processing operation on the first recoverable item wherein the third processing operation is selected from the group consisting of inspecting, testing, and marking. The second kit may include a package, wherein the package contains the first recoverable item and the new item. The second kit may include a sterile barrier package that contains the first recoverable item and the new item. The second kit may include a first sterile barrier package that contains the first recoverable item and a second sterile barrier package that contains the new item. Terminally sterilizing the second kit may include a sterilization process selected from the group consisting of gas sterilization, ethylene oxide sterilization, radiation sterilization, ionizing radiation sterilization, gamma sterilization, e-beam sterilization, and liquid chemical sterilization. Distributing the second kit. Sending the second kit to an end user. Transferring ownership of the second kit to the end user. Transferring ownership of the second kit to the end user may include selling the second kit to the end user.

Another aspect of the technology is a method for recovering at least a portion of a terminally sterilized first kit, wherein the first kit is used in a medical procedure, wherein the first kit includes a first recoverable item, and wherein the first kit is owned by an end user. The method including the steps of: after the first kit is used in the medical procedure, purchasing the first recoverable item from the end user by a purchaser; and receiving the first recoverable item by the purchaser.

Various embodiments of this aspect of the technology may include one or more of the following. The first recoverable item may consist of materials that are impervious to repeated terminal sterilization. The first recoverable item may consist of metal. The first recoverable item may be a medical instrument. Providing a container to receive the first recoverable item after the first kit is used in the medical procedure. The first kit may include the container. The container may be a package that contained the first recoverable item. After receiving the first recoverable item, performing a processing operation on the first recoverable item, wherein the processing operation is selected from the group consisting of receiving, cleaning, disinfecting, sterilizing, inspecting, testing, marking, refurbishing, disassembling, recycling, stocking, and discarding. Performing a processing operation on the first recoverable item may include: performing a first processing operation on the first recoverable item, wherein the first processing operation is selected from the group consisting of cleaning, disinfecting, and sterilizing; performing a second processing operation on the first recoverable item, wherein the second processing operation is selected from the group consisting of refurbishing and recycling; and performing a third processing operation on the first recoverable item wherein the third processing operation is selected from the group consisting of inspecting, testing, and marking. Providing a new item; after performing the processing operation on the first recoverable item, combining the first recoverable item and the new item in a second kit; and terminally sterilizing the second kit. The new item may be a medical implant. After the first kit is used in the medical procedure, receiving a second recoverable item of the first kit for processing; and performing a processing operation on the second recoverable item, wherein the processing operation on the second recoverable item is selected from the group consisting of receiving, cleaning, disinfecting, sterilizing, inspecting, testing, marking, refurbishing, disassembling, recycling, stocking, and discarding. After performing the processing operations on the first and second recoverable items, combining the first and second recoverable items and the new item in the second kit. After the first kit is used in the medical procedure, receiving a first reusable item of the first kit for processing; and performing a processing operation on the first reusable item, wherein the processing operation on the first reusable item is selected from the group consisting of receiving, cleaning, disinfecting, sterilizing, inspecting, testing, marking, refurbishing, recycling, and stocking. After performing the processing operations on the first recoverable item and the first reusable item, combining the first recoverable item, the first reusable item, and the new item in the second kit. The second kit may include a package, wherein the package contains the first recoverable item and the new item. The second kit may include a sterile barrier package, wherein the sterile barrier package contains the first recoverable item and the new item. The second kit may include a first sterile barrier package that contains the first recoverable item and a second sterile barrier package that contains the new item. Terminally sterilizing the second kit may include a sterilization process selected from the group consisting of gas sterilization, ethylene oxide sterilization, radiation sterilization, ionizing radiation sterilization, gamma sterilization, e-beam sterilization, and liquid chemical sterilization. Distributing the second kit. Sending the second kit to an end user. Transferring ownership of the second kit to the end user. Transferring ownership of the second kit to the end user may include selling the second kit to the end user.

Yet another aspect of the technology is a kit for a medical procedure, including: a recovered item; and a new item; a recovery container; wherein the recovered item and the new item are packaged together as a unit and terminally sterilized together after packaging.

Various embodiments of this aspect of the technology may include one or more of the following. The recovered item may bear a mark indicating how many times the recovered item has been recovered. The recovery container and the unit are provided by a common entity, such as a manufacturer. The unit may be further packaged with the recover container. The recovered item may be a reprocessed item. The recovered item may be a refurbished item. The refurbished item may be a medical instrument. The new item may be a medical implant. The recovered item and the new item may be terminally sterilized by a sterilization process selected from the group consisting of gas sterilization, ethylene oxide sterilization, radiation sterilization, ionizing radiation sterilization, gamma sterilization, e-beam sterilization, and liquid chemical sterilization. The kit may include a sterile barrier package containing the recovered item and the new item. The kit may include a first sterile barrier package containing the recovered item; a second sterile barrier package containing the new item; and a package containing the first and second sterile barrier packages. The kit may include a container to receive the recovered item after the kit is used. The kit of may be in combination with a container to receive the recovered item after the kit is used.

Another embodiment may include kit comprising: first medical device, wherein the first medical device is a new medical device having not previously been used in a medical procedure and adapted to engage with an implant or an instrument adapted to engage with a patient's anatomy; a second medical device, wherein the second medical device is a used, non-cutting medical device having been previously used in a prior medical procedure and adapted to engage with an implant or an instrument adapted to engage with a patient's anatomy, wherein subsequent the prior medical procedure the second medical device is recovered and processed such that it may be used again in another medical procedure; a sterile barrier package dimensioned and configured to receive and contain at least one first medical device and at least one second medical device, wherein the first and second medical devices are terminally sterilized after being placed in the sterile barrier package. The first medical device may be adapted and configured to be implanted. The second medical device may be a tool adapted to engage with the first medical device. The first medical device may be adapted and configured to be implanted and wherein the second medical device is a tool adapted to engage with the first medical device.

Another embodiment may include a system comprising a recovery container comprising barrier packaging suitable for shipping a biohazard; and a kit wherein the kit further comprises at least one first medical device, wherein the first medical device is a new medical device having previously not been used in a medical procedure and adapted to engage with an implant or an instrument adapted to engage with a patient's anatomy; at least one second medical device, wherein the second medical device is a used medical instrument having been previously used in a prior medical procedure and adapted to engage with an implant or an instrument adapted to engage with a patient's anatomy; wherein subsequent the prior medical procedure the second medical device is recovered and processed such that it may be used again in another medical procedure, then stored in an inventory location, separate from the first medical device; and an outer package further comprising: a first tray, wherein the first tray contains a plurality of wells; and wherein the first tray contains the first medical device and the second medical device; wherein the first and second medical devices are terminally sterilized after being placed in and sealed within the first tray; and wherein the outer package is sealed after the first tray is inserted within the outer package. The outer package may further comprise a second tray. The recover container may be adapted to be placed in the outer package with the first tray. The recovery container may be a flexible container. One of the first tray or the second tray further comprises a single well and the other of the first tray or the second tray comprises a plurality of wells. The first tray and the second tray may contain a plurality of wells.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings.

DETAILED DESCRIPTION

Figure 1:
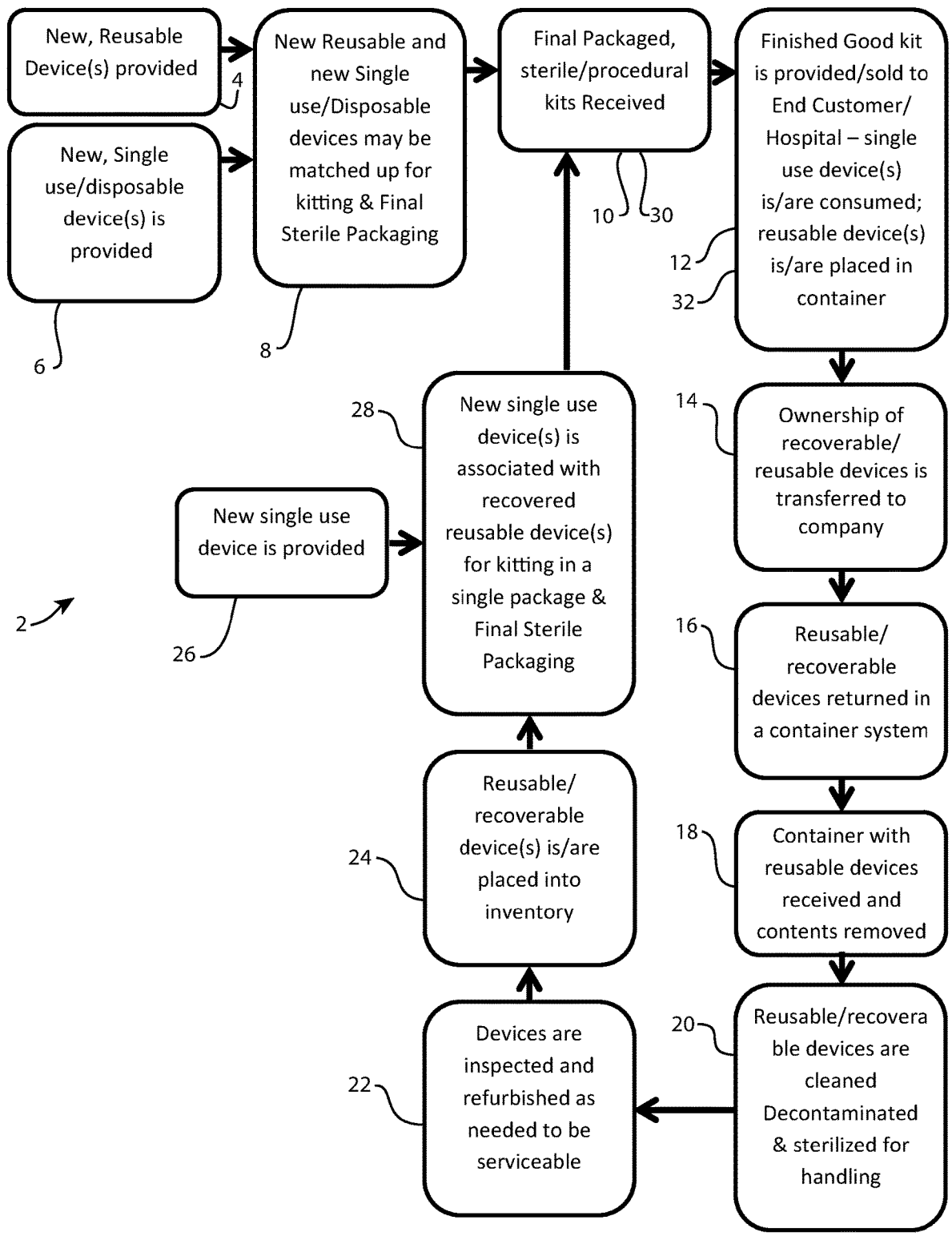
FIG. 1 is a flowchart of a process for building a sterile procedure kit, transferring that kit to a hospital or other end user, obtaining the non-consumed kit components, and reprocessing such components for combination with other single use or consumable devices to be reused as a single sterile kit.

The disclosed technology will be best understood by reference to the drawings, wherein like parts are designated by like numerals throughout. It will be readily understood that the components, assemblies, systems, methods, and processes, as generally described and illustrated herein, could be arranged and designed in a wide variety of different configurations. Thus, the following detailed description of the apparatus, systems, and methods is not intended to limit the scope of the invention, as claimed in this or any other application claiming priority to this application.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

In this specification, the following definitions are used:

New means an item that has never been used in service, for example, used in a medical procedure. The service environment may be, for example, an operating room, a medical procedure room, a surgical environment, and the like. In the context of terminally sterilized items, new also means having been terminally sterilized only once, and never having been removed from the sterile barrier system. In the context of end-user-sterilized items, an item is no longer new after it is exposed to the service environment by removing a sterile barrier protecting the item or by opening a sterilization tray, whether or not the item is actually used in service or not.

Recombine means to combine items, or cause items to combine, again or differently.

Recover means to take possession of or retrieve an item previously provided to another person or entity; to get an item back.

Recycle means to treat or process a used or waste item to make the item or its constituents suitable for reuse.

Refurbish means to return a used item to new condition; to repair and/or make improvements to an item; especially after recovering the item.

Reprocess means to subject a used item to special processing or treatment in preparation for reuse. In this specification, reprocess excludes rework performed during the initial manufacture of a new item.

Reuse means to use an item again, especially after recovering or reprocessing the item.

Terminal sterilization means final clean sterile condition of an item within a sterile barrier system, ready for use in a medical procedure. In this specification, terminal sterilization includes gas sterilization, ethylene oxide sterilization, radiation sterilization, ionizing radiation sterilization, gamma sterilization, e-beam sterilization, and liquid chemical sterilization; and excludes steam sterilization.

As shown in FIG. 1, the disclosed technology may include a process and or system that provides a means for creating a sterile kit and providing that sterile kit to an end user for consumption of certain components of the kit. The contents of the kit may vary depending on the type of procedure to be performed. During the initial use of the kit, certain components may be consumed while other components may not be consumed, but may have been utilized during the procedure. For example, an implant is consumed by being permanently or semipermanently installed on or in a patient, while a drill guide may be used during a procedure and may remain usable after the procedure. Still further, certain components of the kit may not have been used or consumed. Typical non-consumable components for the system may be drills, reamers, and other instruments; typical consumed devices may be implants. However, multiple implants could be provided and the unused implants could be recovered and reprocessed for placement in a new kit.

The process provides a means for transferring ownership of the non-consumed components to an entity such as a manufacturer which may or may not be the original manufacturer. Once a sterile kit is purchased by the hospital or end customer, that kit becomes the property of that facility. In order to reclaim the unused or non-consumed components and/or devices for re-use, the ownership of those components may be transferred to a manufacturer or back to the original manufacturer by a repurchase, rebate, refund of deposit, or other legally acceptable means. If ownership is not transferred to a manufacturer or back to the original manufacturer, ownership of those items remains with the end customer. The transfer of ownership to a manufacturer or back to the original manufacturer may provide the end customer with an additional source of income while also allowing the manufacturer to reduce their cost of goods.

The recovered or non-consumed components may be stored and transported in a container or container system. The container may be included with the kit or placed in a variety of locations, including but not limited to the surgical suite, central supply or other convenient locations. The container may accumulate recovered or non-consumed components from a single medical procedure, or from multiple medical procedures. The container with recovered or non-consumed kit components may be transferred and or transported to a manufacturer. The contents of the container may then be processed for safe handling (e.g. cleaned and sterilized) then refurbished or reprocessed. This may also be advantageous in ensuring that the components and or devices that were not consumed are optimized for their intended function. This process provides the opportunity for each component and or device to undergo a quality control step after each use.

The refurbished components may then be transferred to an inventory location until they are needed for assembly of new kits, or the refurbished components may be immediately used in the assembly of new kits. The reused/recovered or refurbished components may then be combined with new single use or consumable product(s) in a kit that may then be packaged and sterilized for use as a sterile kit. The sterile kit may be dedicated to a particular surgical procedure, such as hammertoe correction or mandibular reconstruction. The system and or process of the disclosed technology may provide a sterile, surgical kit that may contain new, single use or consumable components in combination with reprocessed or refurbished reusable/non-consumable components.

One aspect of the system of the disclosed technology may comprise the sterile kit, the container, and the process of recombining non-consumable device(s) with a new consumable device(s) in a new kit having a shared or common sterile barrier.

The system and process of the disclosed technology are advantageous as they may provide better means for determining inventory utilization and determination of a device's useful life expectancy. The disclosed technology may also provide advantages to the end user by reducing medical waste and related costs, increasing operational efficiencies, and or by providing the end user with a means for offsetting the cost or generating income from components and or devices that would otherwise have been discarded. The manufacturer may also benefit from the disclosed technology by having a means to lower operational cost and costs of goods by procuring the non-consumable component or components from the end user at a lower cost than purchasing newly manufactured components, not to mention conserving materials, thereby avoiding the negative environmental consequences of raw material extraction and refinement.

Additional benefits of the disclosed technology may include the ability to provide, in a sterile single-use kit, robust components or instrumentation of durable material and quality of construction that may perform better than traditional sterile packaged disposable components that are typically constructed of material and by methods that are conducive to lower manufacturing costs and quality resulting in items of compromised durability.

Referring to FIG. 1, a process or method 2 may include any or all of the following steps in any order:

Step 4, providing a new reusable device.

Step 6, providing a new first single-use device.

Step 8, combining the reusable device, the new first single-use device, and a first package into a first kit. Step 8 may include sterilizing the first kit, or sterilizing the first kit may be a separate step.

Step 10, receiving the first kit by an owner such as a medical facility or an end user.

Step 12, transferring ownership of the first kit to the owner, wherein a medical procedure is performed during the end user's ownership of the first kit, wherein the reusable device is used during the medical procedure, wherein the first single-use device is consumed during the medical procedure, wherein the reusable device is placed in a container after the medical procedure ends.

Step 14, transferring ownership of at least a portion of the first kit to an entity such as a processor, a second manufacturer, or the original manufacturer, wherein the transferred portion of the first kit includes the reusable device, wherein ownership of the first package and/or the container may also be transferred to the entity.

Step 16, transporting the container and the reusable device to a facility of the entity. The first package may also be transported.

Step 18, opening the container and removing the contents. Step 18 may include segregating the reusable device from any other contents of the container. The first package may also be segregated. Segregating may be a separate step.

Step 20, cleaning, disinfecting, and/or sterilizing the reusable device. The first package may also be cleaned, disinfected, and/or sterilized. The purpose of this sterilization operation is to render the items safe for handling during subsequent processing operations prior to terminal sterilization.

Step 22, inspecting and/or testing the reusable device. The first package may also be inspected and/or tested. Step 22 may also include refurbishing the reusable device, wherein refurbishing may include replacing a part of the reusable device, sharpening the reusable device, refinishing the reusable device, and the like. The first package may also be refurbished. Refurbishing may be a separate step. Refurbishing may occur in more than one step or operation. Inspection and/or testing may precede refurbishing, in order to determine the refurbishment needs of an item. Inspection and/or testing may also follow refurbishing, in order to prove that the item meets service requirements.

Step 24, placing the refurbished reusable device into an inventory storage location. The first package may also be placed into inventory.

Step 26, providing a new second single-use device.

Step 28, combining the refurbished reusable device, the new second single-use device, and a second package into a second kit. The second package may be a first package from inventory. Step 28 may include sterilizing the second kit, or sterilizing the second kit may be a separate step.

Step 30, receiving the second kit by an owner. At this step, the owner may be the same as the owner of the first kit, or different.

Step 32, transferring ownership of the second kit to the owner.

Figure 2:
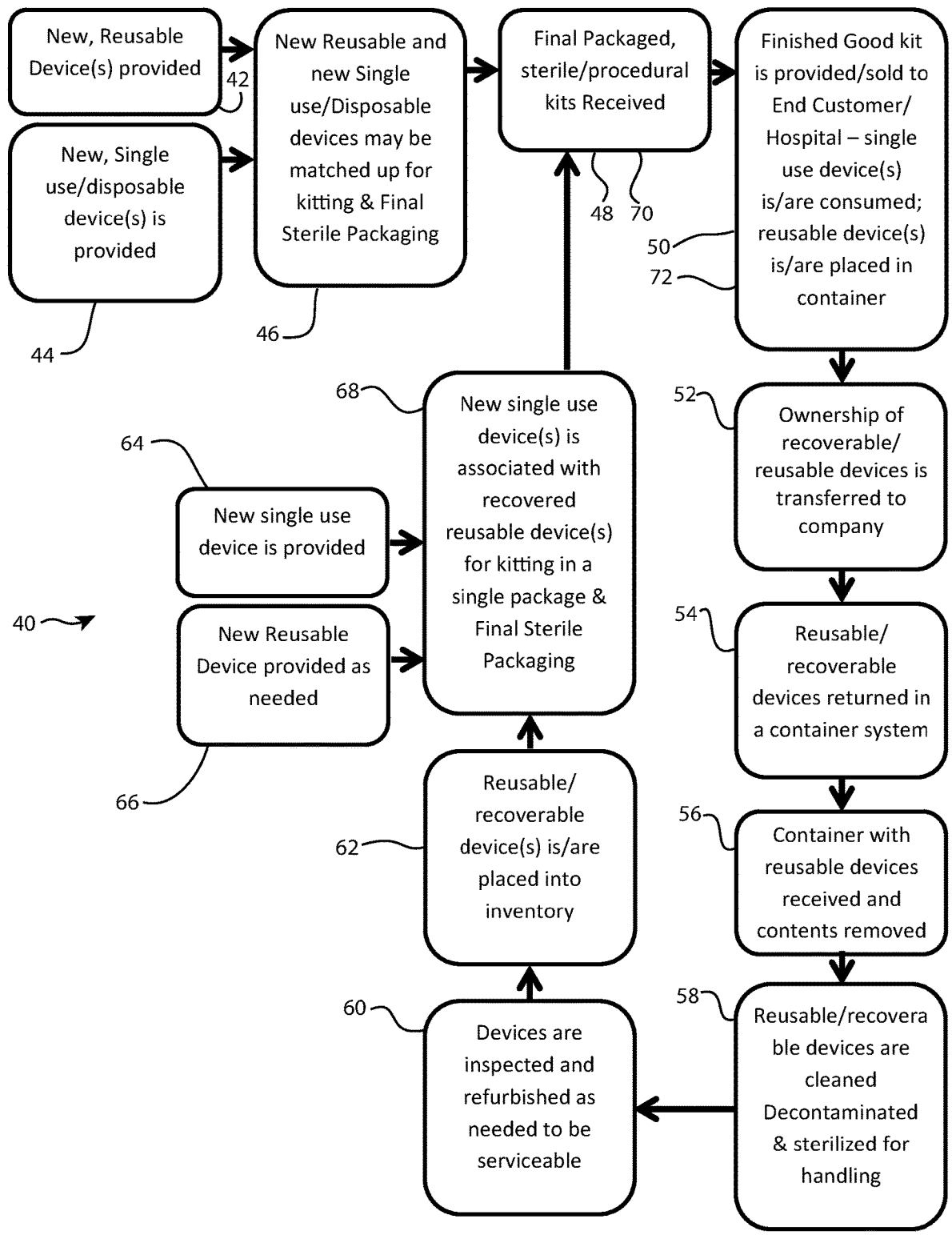
FIG. 2 is a flowchart of another process for building a sterile procedure kit, transferring that kit to a hospital or other end user, obtaining the non-consumed kit components, and reprocessing such components for combination with other new single use or consumable devices and other non-consumable or reusable devices to be reused as a single sterile kit.

As shown in FIG. 2, the disclosed technology may include a process and or system that provides a means for creating a sterile kit and providing that sterile kit to an end user for consumption of certain components of the kit. The contents of the kit may be specific to a particular type of procedure to be performed and may be referred to as a procedural kit; various procedural kits are envisioned, each kit tailored to a specific procedure. During the initial use of the kit, certain components may be consumed while other components may not be consumed, but may have been utilized during the procedure. Still further, certain components of the kit may not have been used or consumed.

The process provides a means for transferring ownership of the non-consumed components to a manufacturer which may or may not be the original manufacturer. Once a sterile kit is purchased by the hospital or end customer, that kit becomes the property of that facility. In order to reclaim the unused or non-consumed components and/or devices for re-use, the ownership of those components may be transferred to a manufacturer or back to the original manufacturer by a repurchase, rebate, refund of deposit, or other legally acceptable means. If ownership is not transferred to a manufacturer or back to the original manufacturer, ownership of those items remains with the end customer. The transfer of ownership to a manufacturer or back to the original manufacturer may provide the end customer with an additional source of income while also allowing the manufacturer to reduce their cost of goods.

The recovered or non-consumed components may be stored and transported in a container or container system. The container with recovered or non-consumed kit components may be transferred and or transported to a manufacturer. The contents of the container may then be processed for safe handling (e.g. cleaned and sterilized) then refurbished or reprocessed. This may also be advantageous in ensuring that the components and or devices that were not consumed are optimized for their intended function. This process provides the opportunity for each component and or device to undergo a quality control step after each use.

The refurbished components may then be transferred to an inventory location until they are needed for assembly of new kits, or the refurbished components may be immediately used in the assembly of new kits. The reused/recovered or refurbished components may then be combined with new single use or consumable devices or product(s) and other non-consumable or reusable devices or product in a kit that may then be packaged and sterilized for use as a sterile kit that may be used for a particular surgical procedure. The system and or process of the disclosed technology may provide a sterile, surgical kit that may contain new, single use or consumable components in combination with reprocessed or refurbished or new reusable/non-consumable components. Typical non-consumable components for the system may be drills, reamers, and other instruments; typical consumed devices may be implants or other single use disposable items. However, multiple implants could be provided and the unused implants could be recovered and reprocessed for placement in a new kit.

The disclosed technology may also provide a container or container system that may allow the non-consumed components to be collected, stored, and or transported. The container may be placed in a variety of locations, include but not limited to the surgical suite, central supply or other convenient locations.

The system and process of the disclosed technology are advantageous as they may provide a better means for determining inventory utilization and determination of a devices useful life expectancy. The disclosed technology may also provide advantages to the end user by reducing medical waste and related cost, increasing operational efficiencies, limiting cross-contamination, improving sterility assurance at the time of use, improving cleanliness of kit items, and or by providing the end user with a means for offsetting the cost or generating income from components and or devices that would otherwise have been discarded. The manufacturer may also benefit from the disclosed technology by having a means to lower operational cost and costs of goods by procuring the non-consumable component(s) from the end user at a lower cost than purchasing newly manufactured components, not to mention conserving materials, thereby avoiding the negative environmental consequences of raw material extraction and refinement.

Additional benefits of the disclosed technology may include the ability to provide robust components or instrumentation of durable material and quality of construction that may perform better than traditional sterile packaged components that are typically constructed of material and by methods that are conducive to lower manufacturing costs and quality resulting in items of compromised durability.

The process and system of the disclosed technology may have the further benefit that the original equipment manufacturer may be the holder of the required regulatory approvals necessary to combine the consumable device(s) or component(s) (e.g. the implant) with the reusable or non-consumable component(s) or device(s). The original manufacturer may be the preferred entity capable of combining the consumable or implant with the non-consumable component(s) or device(s) due to the potential regulatory clearances or approvals that may be required.

Referring to FIG. 2, a process 40 may include any or all of the following steps in any order:

Step 42, providing a new first reusable device.

Step 44, providing a new first single-use device.

Step 46, combining the first reusable device, the first single-use device, and a first package into a first kit. Step 46 may include sterilizing the first kit, or sterilizing the first kit may be a separate step.

Step 48, receiving the first kit by an owner, such as a medical facility or an end user.

Step 50, transferring ownership of the first kit to the owner, wherein a medical procedure is performed during the end user's ownership of the first kit, wherein the first reusable device is used during the medical procedure, wherein the first single-use device is consumed during the medical procedure, wherein the first reusable device is placed in a container after the medical procedure ends.

Step 52, transferring ownership of at least a portion of the first kit to an entity such as a processor, a second manufacturer, or the original manufacturer, wherein the transferred portion of the first kit includes the first reusable device, wherein ownership of the first package and/or the container may also be transferred to the entity.

Step 54, transporting the container and the first reusable device to a facility of the entity. The first package may also be transported.

Step 56, opening the container and removing the contents. Step 56 may include segregating the reusable device from any other contents of the container. The first package may also be segregated. Segregating may be a separate step.

Step 58, cleaning, disinfecting, and/or sterilizing the first reusable device. The first package may also be cleaned, disinfected, and/or sterilized. The purpose of this sterilization operation is to render the items safe for handling during subsequent processing operations prior to terminal sterilization.

Step 60, inspecting and/or testing the first reusable device. The first package may also be inspected and/or tested. Step 60 may also include refurbishing the first reusable device, wherein refurbishing may include replacing a part of the first reusable device, sharpening the first reusable device, refinishing the first reusable device, and the like. The first package may also be refurbished. Refurbishing may be a separate step. Refurbishing may occur in more than one step or operation. Inspection and/or testing may precede refurbishing, in order to determine the refurbishment needs of an item. Inspection and/or testing may also follow refurbishing, in order to prove that the item meets service requirements.

Step 62, placing the refurbished first reusable device into an inventory storage location.

The first package may also be placed into inventory.

Step 64, providing a new second single-use device.

Step 66, providing a new second reusable device.

Step 68, combining the refurbished first reusable device, the second single-use device, the second reusable device, and a second package into a second kit. The second package may be a first package from inventory. Step 68 may include sterilizing the second kit, or sterilizing the second kit may be a separate step.

Step 70, receiving the second kit by an owner. At this step, the owner may be the same as the owner of the first kit, or different.

Step 72, transferring ownership of the second kit to the owner such as a medical facility or an end user.

Figure 3:
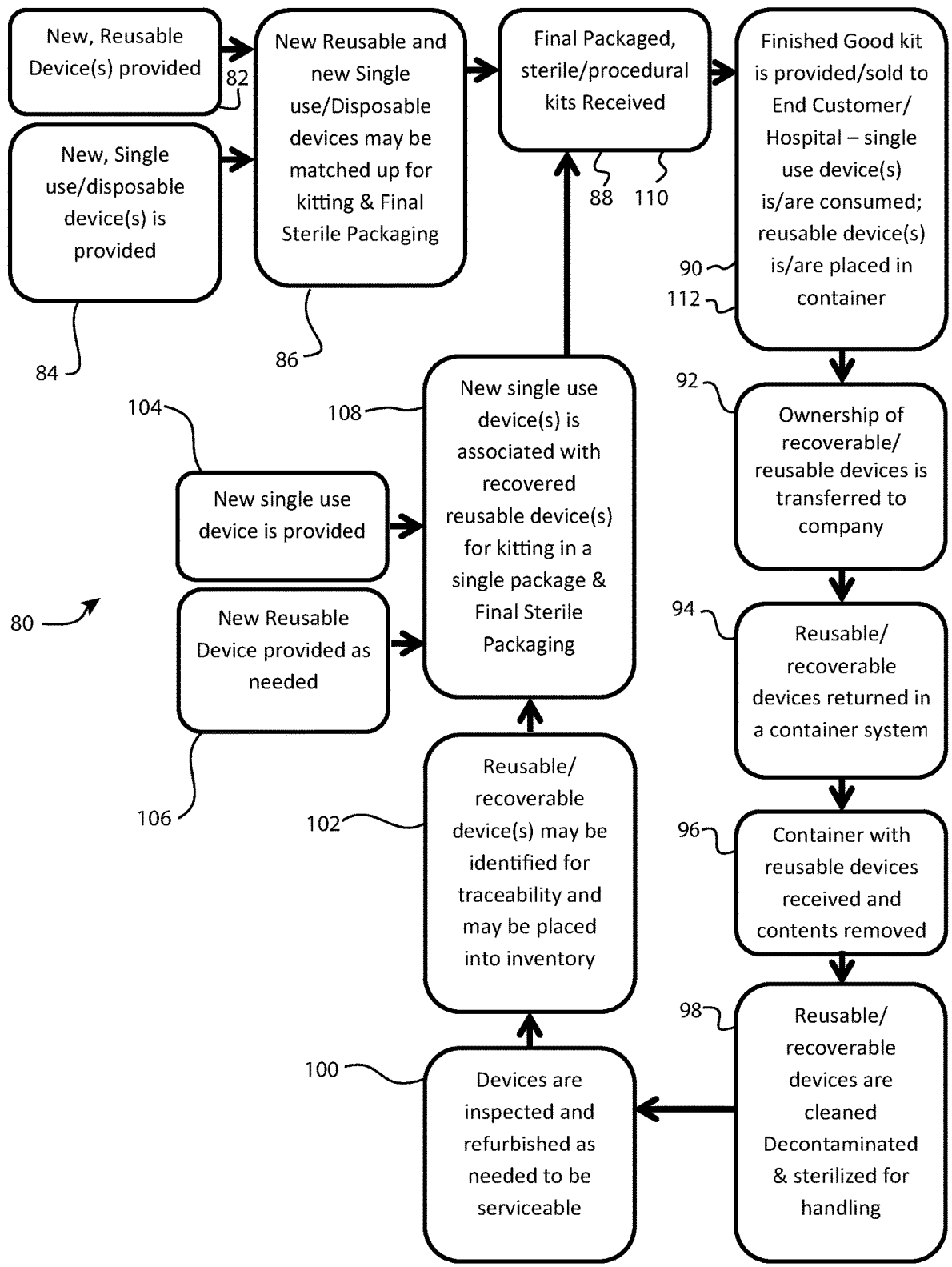
FIG. 3 is a flowchart of yet another process for building a sterile procedure kit, transferring that kit to a hospital or other end user, obtaining the non-consumed kit components, and reprocessing such components and identifying those components for traceability and for combining with other new single use or consumable devices and other non-consumable or reusable devices to be reused as a single sterile kit.

FIG. 3 depicts a system or process of the disclosed technology that is similar to that represented in FIGS. 1 and 2. However, this third embodiment may include a step in the reprocessing that may add or modify the reprocessed component or devices in such a way as to enhance the traceability of that particular component or device. In addition to the merits of the disclosed technology discussed herein, this particular step may be advantageous in further enhancing the determination of inventory utilization and or the useful service life of the component and or device.

Referring to FIG. 3, a process 80 may include any or all of the following steps in any order:

Step 82, providing a new first reusable device.

Step 84, providing a new first single-use device.

Step 86, combining the first reusable device, the first single-use device, and a first package into a first kit. Step 86 may include sterilizing the first kit, or sterilizing the first kit may be a separate step.

Step 88, receiving the first kit by an owner such as a medical facility or an end user.

Step 90, transferring ownership of the first kit to the owner, wherein a medical procedure is performed during the end user's ownership of the first kit, wherein the first reusable device is used during the medical procedure, wherein the first single-use device is consumed during the medical procedure, wherein the first reusable device is placed in a container after the medical procedure ends.

Step 92, transferring ownership of at least a portion of the first kit to an entity such as a processor, a second manufacturer, or the original manufacturer, wherein the transferred portion of the first kit includes the first reusable device, wherein ownership of the first package and/or the container may also be transferred to the entity.

Step 94, transporting the container and the first reusable device to a facility of the processor, the second manufacturer, or the original manufacturer. The first package may also be transported.

Step 96, opening the container and removing the contents. Step 96 may also include segregating the first reusable device from any other contents of the container. The first package may also be segregated. Segregating may be a separate step.

Step 98, cleaning, disinfecting, and/or sterilizing the first reusable device. The first package may also be cleaned, disinfected, and/or sterilized. The purpose of this sterilization operation is to render the items safe for handling during subsequent processing operations prior to terminal sterilization.

Step 100, inspecting and/or testing the first reusable device. The first package may also be inspected and/or tested. Step 100 may also include refurbishing the first reusable device, wherein refurbishing may include replacing a part of the first reusable device, sharpening the first reusable device, refinishing the first reusable device, and the like. The first package may also be refurbished. Refurbishing may be a separate step. Refurbishing may occur in more than one step or operation. Inspection and/or testing may precede refurbishing, in order to determine the refurbishment needs of an item. Inspection and/or testing may also follow refurbishing, in order to prove that the item meets service requirements.

Step 102, identifying the first reusable device, wherein identification may be for traceability or to denote the number of refurbishment cycles undergone by the first reusable device. The first package may also be identified. Identification may include marking the first reusable device and/or the first package. Step 102 may include placing the refurbished first reusable device into an inventory storage location. The first package may also be placed into inventory. Placing items into inventory may be a separate step.

Step 104, providing a new second single-use device.

Step 106, providing a new second reusable device.

Step 108, combining the refurbished first reusable device, the second single-use device, the second reusable device, and a second package into a second kit. The second package may be a first package from inventory. Step 108 may include sterilizing the second kit, or sterilizing the second kit may be a separate step.

Step 110, receiving the second kit by an owner. At this step, the owner may be the same as the owner of the first kit, or different.

Step 112, transferring ownership of the second kit to the owner.

Figure 4:
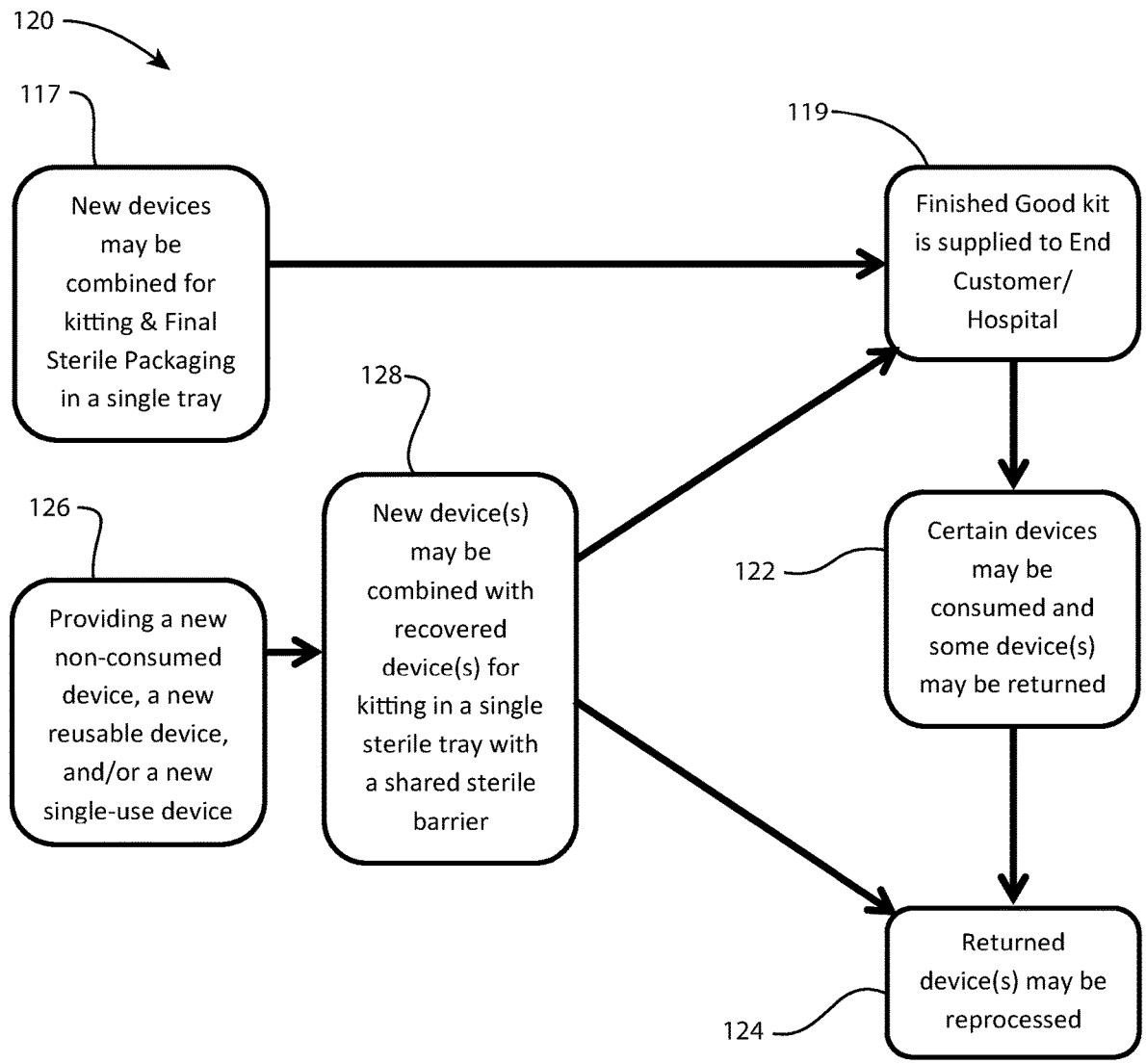
FIG. 4 is a flowchart of yet another process of building a sterile procedure kit in a single tray, transferring that kit to a hospital or other end user, reprocessing certain non-consumed components, and combining with other new devices for kitting in a sterile tray with a shared sterile barrier.
Figure 5:
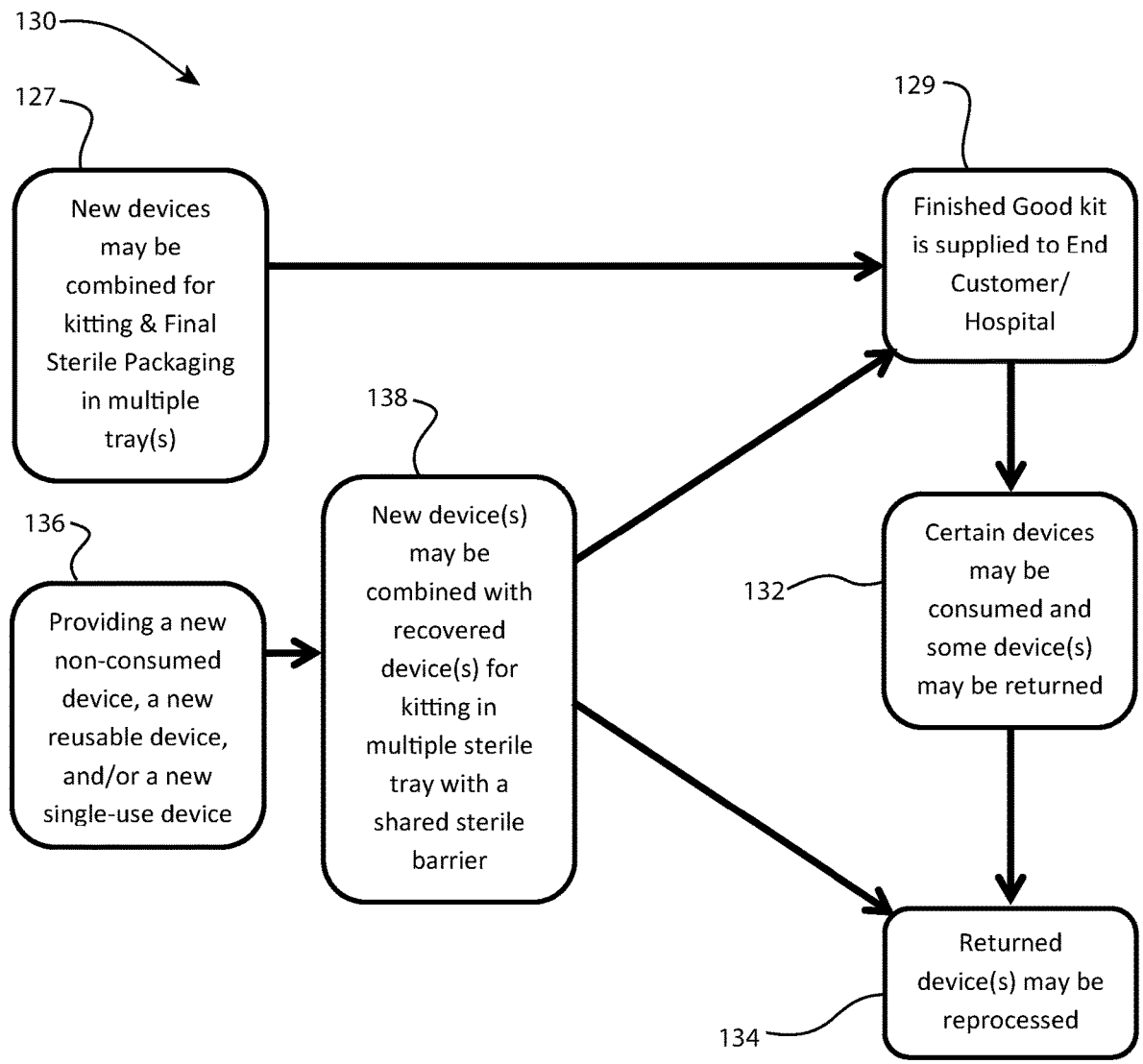
FIG. 5 is a flowchart of yet another process of building a sterile procedure kit in a tray(s), transferring that kit to a hospital or other end user, reprocessing certain non-consumed components, and combining with other new devices for kitting in a sterile tray with a shared sterile barrier.

As shown in FIGS. 4 and 5, the disclosed technology may include a process and or system that provide a means for obtaining non-consumed and or reusable and or non-consumable component(s) and or devices from a single kit or multiple kits. Those components and or devices may or may not require reprocessing or refurbishing. The non-consumed and or non-consumable and or reusable components or devices may then be combined with other new devices of varying sorts into a sterile kit that may or may not have multiple trays and having one common sterile barrier or common packaging barrier. The system and or process of the disclosed technology may provide a sterile, surgical kit that may contain new, single use or consumable components in combination with or without new reusable/non-consumable components in combination with or without reprocessed or refurbished or reusable/non-consumable components.

The disclosed technology may also provide a container or container system that may allow the non-consumed components to be stored and or transported. The container may be placed in a variety of locations, include but not limited to the surgical suite, central supply or other convenient locations.

The system and process of the disclosed technology are advantageous as it may provide a better means for determining inventory utilization and determination of a device's useful life expectancy. The disclosed technology may also provide advantages to the end user by reducing medical waste and related cost, increasing operational efficiencies and or by providing the end user with a means for generating income from components and or devices that would otherwise have been discarded. The manufacturer may also benefit from the disclosed technology by having a means to lower operational cost and costs of goods by procuring the non-consumable component(s) from the end user at a lower cost than purchasing newly manufactured components.

Additional benefits of the disclosed technology may include the ability to provide robust components or instrumentation of durable material and quality of construction that may perform better than traditional sterile packaged components that are typically constructed of material and by methods that are conducive to lower manufacturing costs and quality resulting in items of compromised durability.

Referring to FIG. 4, a process 120 may include any or all of the following steps in any order:

Step 122, obtaining a first non-consumed device. The first non-consumed device may be obtained from a first kit. Step 122 may include obtaining a first reusable device. The first reusable device may be obtained from the first kit or a second kit. Obtaining the first reusable device may be a separate step.

Step 124, reprocessing the first non-consumed device and/or the first reusable device. Step 124 may include refurbishing the first reusable device. The first non-consumed device may also be refurbished. Refurbishing may be a separate step.

Step 126, providing a new second non-consumed device, a new second reusable device, and/or a new single-use device.

Step 128, combining the first non-consumed device, the new second non-consumed device, the first reusable device, the new second reusable device, and/or the new single-use device with a first tray of a sterile barrier system into a third kit.

FIG. 4 also illustrates steps 117 and 119 which may precede the steps 122-128 listed above for process 120. Step 117 is combining new devices in a single tray of a sterile barrier system of a kit, such as the first kit or the second kit of process 120. Step 119 is supplying the kit to a customer, such as an end user or medical facility. A medical procedure is performed while the customer has the kit.

Referring to FIG. 5, a process 130 may include any or all of the following steps in any order:

Step 132 obtaining a first non-consumed device. The first non-consumed device may be obtained from a first kit. Step 132 may include obtaining a first reusable device. The first reusable device may be obtained from the first kit or a second kit. Obtaining the first reusable device may be a separate step.

Step 134, reprocessing the first non-consumed device and/or the first reusable device. Step 134 may include refurbishing the first reusable device. The first non-consumed device may also be refurbished. Refurbishing may be a separate step.

Step 136, providing a new second non-consumed device, a new second reusable device, and/or a new single-use device.

Step 138, combining the first non-consumed device, the new second non-consumed device, the first reusable device, the new second reusable device, and/or the new single-use device with a first tray and a second tray into a third kit. The first and second trays may have one common sterile barrier and/or one common packaging barrier.

FIG. 5 also illustrates steps 127 and 129 which may precede the steps 132-138 listed above for process 130. Step 127 is combining new devices in multiple trays of a sterile barrier system of a kit, such as the first kit or the second kit of process 130. Step 129 is supplying the kit to a customer, such as an end user or medical facility. A medical procedure is performed while the customer has the kit.

Figure 6:
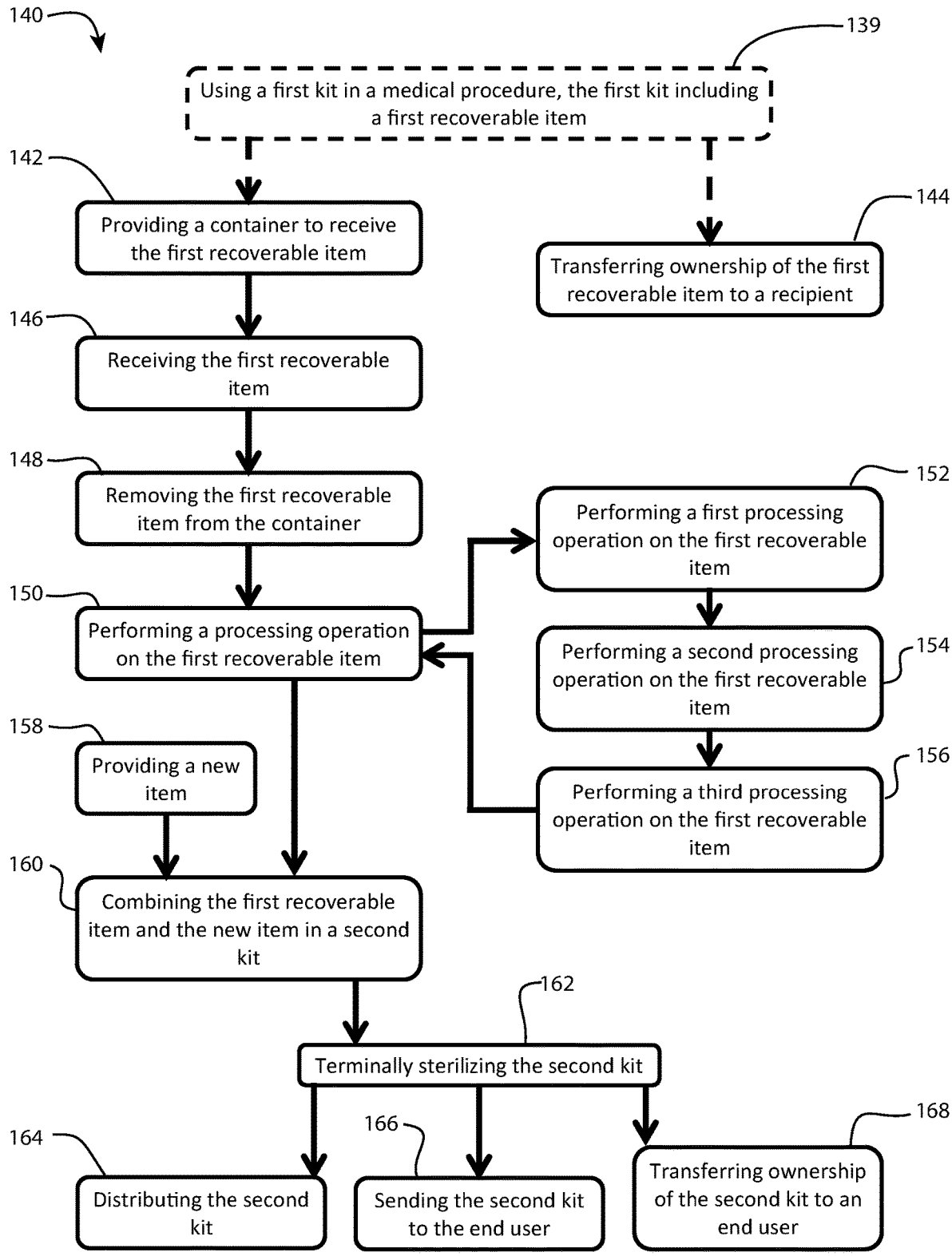
FIG. 6 is a flowchart of yet another process of building a sterile kit.

Referring to FIG. 6, a process 140 may include any or all of the following steps in any order:

Step 142, providing a container to receive a first recoverable item.

Step 144, transferring ownership of the first recoverable item to a recipient.

Step 146, receiving the first recoverable item.

Step 148, removing the first recoverable item from the container.

Step 150, performing a processing operation on the first recoverable item.

Step 152, performing a first processing operation on the first recoverable item.

Step 154, performing a second processing operation on the first recoverable item.

Step 156, performing a third processing operation on the first recoverable item.

Step 158, providing a new item.

Step 160, combining the first recoverable item and the new item in a second kit.

Step 162, terminally sterilizing the second kit.

Step 164, distributing the second kit.

Step 166, sending the second kit to the end user.

Step 168, transferring ownership of the second kit to an end user.

FIG. 6 also illustrates a step 139 which may precede the steps 142-168 listed above for process 140. Step 139 is using a first kit in a medical procedure, the first kit including the first recoverable item. Step 139 is indicated in dashed lines because this step may occur outside the scope of process 140.

A basic version of process 140 may include steps 146, 150, 158, 160, and 162. Step 146 may occur after step 139; steps 146, 150, 160, and 162 may occur in order; and step 158 may precede step 160. Steps 142, 144, 148, 152, 154, 156, 164, 166, and 168 may be optional steps of process 140.

Step 142 may precede, occur simultaneously with, or follow step 139.

The container of step 142 receives the first recoverable item, protects the first recoverable item from damage during transit, and protects anyone handling the container from exposure to the first recoverable item or other contents of the container. The container may provide a biohazard barrier. The container may be a package, carton, or box that contained the first recoverable item and/or the first kit. The container may be provided as part of the first kit, independent from any of the packaging of the first kit. The container may be a pouch, bag, envelope, or other item supplied as part of the first kit, sized to hold recoverable items of the first kit. The container may be supplied independently of the first kit, and may be a box, bin, receptacle, drum, or the like that is sized to hold numerous recoverable items from multiple kits. The container may be reusable. The container may include a locking mechanism so that the container can be locked and unlocked.

The first recoverable item of step 142 is a non-consumed item such as a non-selected implant, an instrument, or an accessory for the medical procedure. The first recoverable item may be a reusable item that is included in the second kit after being refurbished. The first recoverable item may be made entirely of materials that are impervious to repeated terminal sterilization cycles. For example, the first recoverable item may be all metal. The first recoverable item may be recovered so that it can be recycled at the sub-assembly, component part, or raw material level. In this situation, the first recoverable item may include some materials that deteriorate when exposed to repeated terminal sterilization cycles. Under certain circumstances, the first recoverable item may be recovered so that it can be discarded.

Step 144 may occur after step 139. Step 144 may occur at about the same time as steps 142 and/or 146. Step 144 may precede, occur simultaneously with, or follow steps 142 and/or 146. Step 144 may involve a recipient buying the first recoverable item from an owner of the first recoverable item and/or the first kit. The recipient may be a processor, a second manufacturer, or the original manufacturer of the first recoverable item and/or the first kit.

Step 148 may occur before step 150. Step 148 may include segregating the first recoverable item from other contents of the container, which may be waste.

Step 150 may include receiving, cleaning, disinfecting, sterilizing, inspecting, testing, marking, refurbishing, recycling, or stocking the first recoverable item. Step 150 may include steps 152, 154, and/or 156.

Step 152 may include cleaning, disinfecting, or sterilizing the first recoverable item. The purpose of this sterilization operation is to render the first recoverable item safe for handling during subsequent processing operations prior to terminal sterilization.

Step 154 may include refurbishing or recycling the first recoverable item. Refurbishing may include sharpening, straightening, calibrating, polishing, passivating, and/or other tasks. Refurbishing may include partial or complete disassembly of the first recoverable item, replacement of at least one component part, and partial or complete reassembly of the first recoverable item.

Step 156 may include inspecting, testing, or marking the first recoverable item. Marking may indicate the number of times the first recoverable item has been refurbished and/or terminally sterilized. Steps 154 and 156 may occur in any order, and process 140 may include multiple instances of steps 154 and/or 156.

The new item of step 158 may be a consumed item or a non-consumed item. The new item may be an implant.

The second kit of step 160 may include a package that contains the first recoverable item and the new item. The package may be a single sterile barrier package or system that contains the first recoverable item and the new item. The package may also be a box or carton that contains one or more sterile barrier packages. The first recoverable item may be contained in a first sterile barrier package and the new item may be contained in a second sterile barrier package. The first and second sterile barrier packages may both be contained in a box, carton, or other outer package.

Step 162 may include gas sterilization, ethylene oxide sterilization, radiation sterilization, ionizing radiation sterilization, gamma sterilization, e-beam sterilization, or liquid chemical sterilization. Step 162 does not include steam sterilization.

Step 164 may involve sending the second kit to a distributor.

Step 166 may involve sending the second kit directly to an end user or a facility in which medical procedures are performed.

Step 168 may involve selling the second kit to the end user or the facility.

Figure 7:
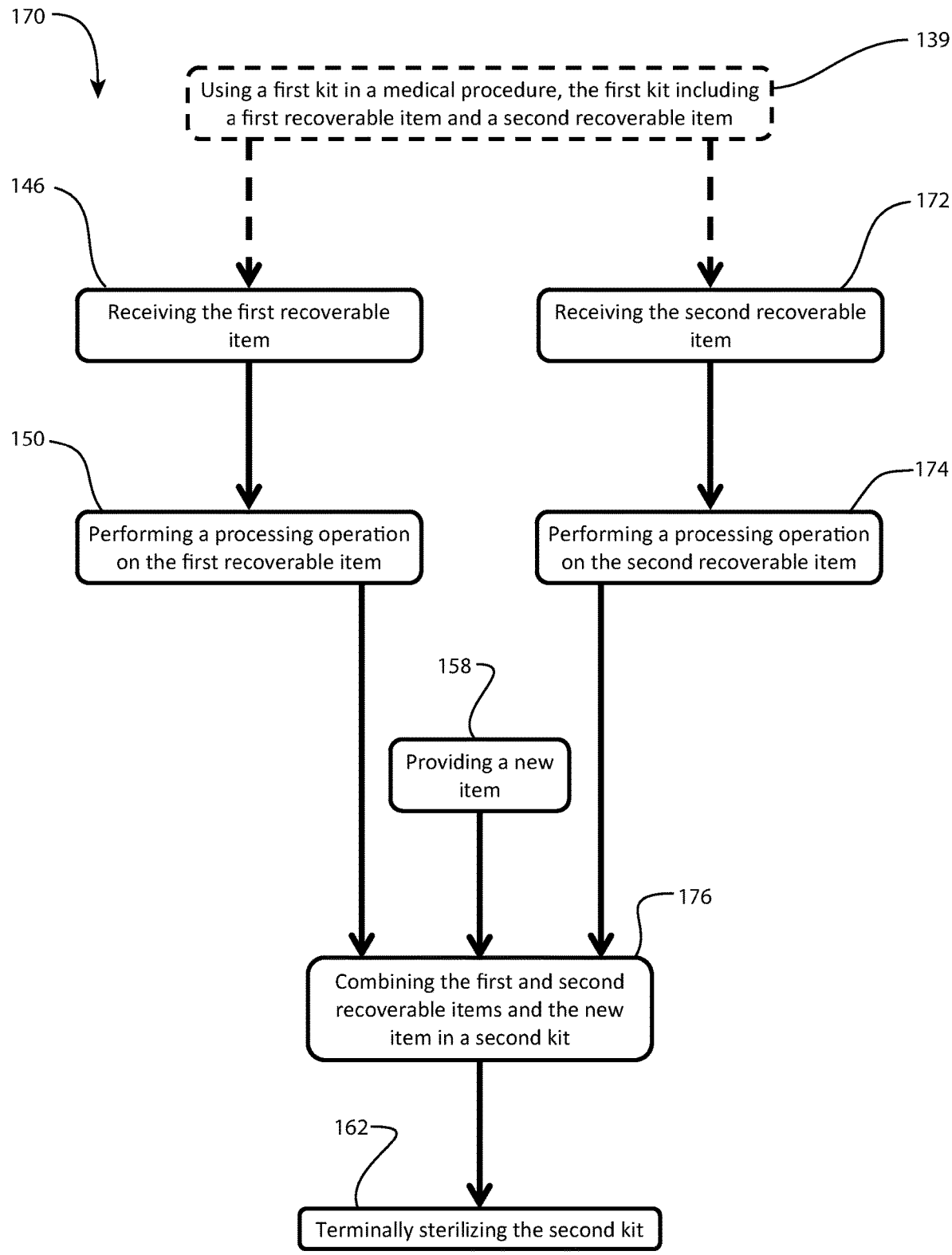
FIG. 7 is a flowchart of a variation of the process of FIG. 6, including a second recoverable item.

Referring to FIG. 7, a process 170 is a variation of process 140 in which a second recoverable item is recovered from the first kit in addition to the first recoverable item. Process 170 may include any or all of the following steps, in any order, in addition to at least the basic steps 146, 150, 158, and 162 of process 140:

Step 172, receiving the second recoverable item.

Step 174, performing a processing operation on the second recoverable item.

Step 176, combining the first recoverable item, the second recoverable item, and the new item in a second kit.

A basic version of process 170 may include steps 146, 150, 158, 162, 172, and 174. Steps 146 and 172 may occur after step 139; steps 146 and 150 may occur in order; steps 172 and 174 may occur in order; steps 150, 158, and 174 may precede step 176; and steps 176 and 162 may occur in order. Step 176 may be optional, at least as step 176 relates to the second recoverable item. Process 170 may also include one or more of the optional steps 142, 144, 148, 152, 154, 156, 164, 166, and 168 of process 140. The optional steps of process 140 may involve the first recoverable item and/or the second recoverable item.

Step 174 may include receiving, cleaning, disinfecting, sterilizing, inspecting, testing, marking, refurbishing, disassembling, recycling, stocking, or discarding the second recoverable item. Step 174 may also include steps 152, 154, and/or 156 performed on the second recoverable item.

However, step 174 may involve a different operation than step 150. For example, the first recoverable item may be refurbished, while the second recoverable item may be recycled at the sub-assembly, component part, or raw material level. In another example, the first recoverable item may be disinfected or sterilized to render the first recoverable item safe for handling during subsequent processing operations prior to terminal sterilization, while the second recoverable item may be recycled or discarded without being disinfected or sterilized. The differences between steps 150 and 174 may be due to differences between the first recoverable item and the second recoverable item, such as the first recoverable item being a reusable item and the second recoverable item being a recyclable item. However, in some situations, neither the first nor the second recoverable item is reusable, and the differences between steps 150 and 174 may be due to differences in the design or materials of the first versus the second recoverable item.

Figure 8:
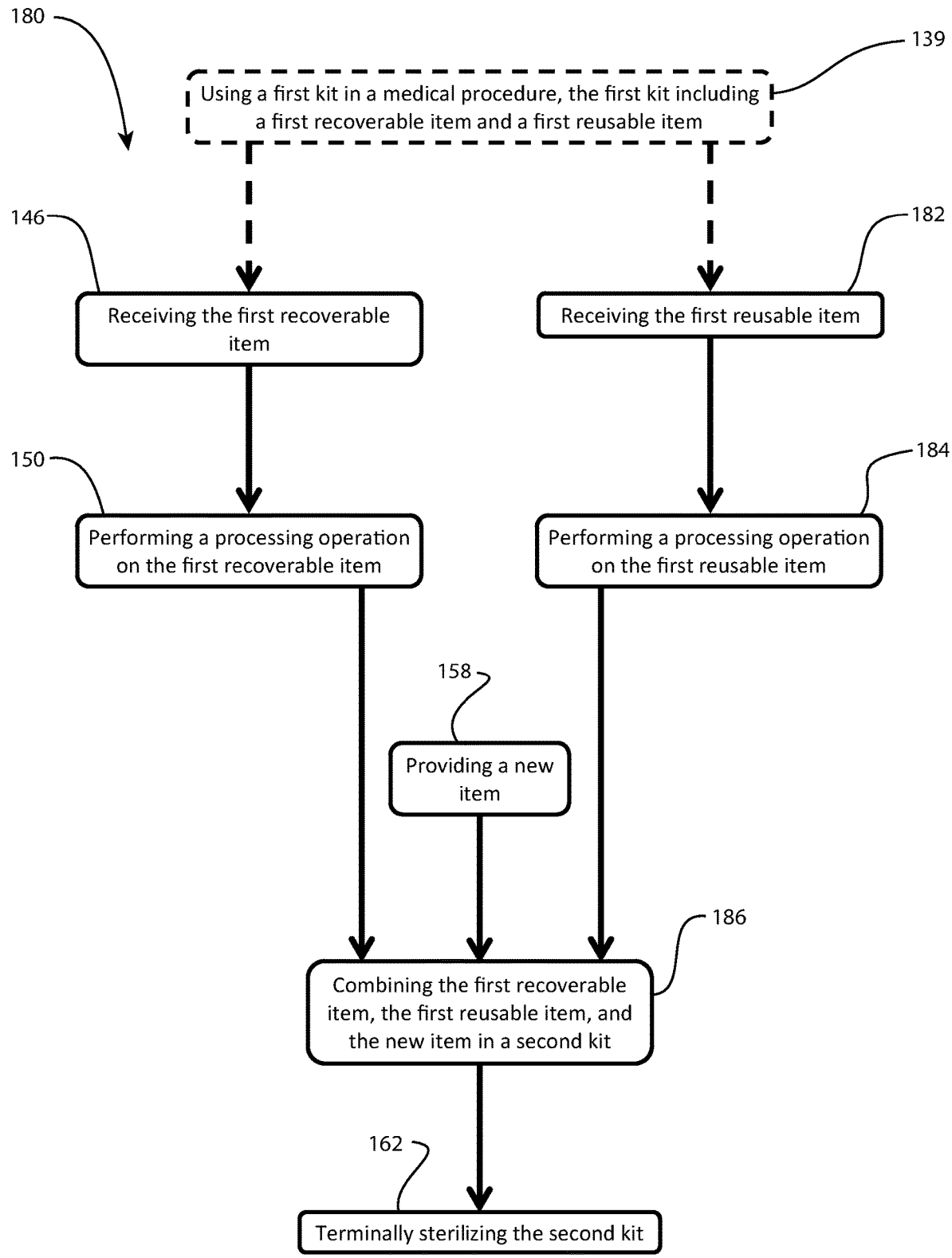
FIG. 8 is a flowchart of another variation of the process of FIG. 6, including a first reusable item.

Referring to FIG. 8, a process 180 is a variation of process 140 in which a first reusable item is recovered from the first kit in addition to the first recoverable item. Process 180 may include any or all of the following steps, in any order, in addition to at least the basic steps 146, 150, 158, and 162 of process 140:

Step 182, receiving the first reusable item.

Step 184, performing a processing operation on the first reusable item.

Step 186, combining the first recoverable item, the first reusable item, and the new item in a second kit.

A basic version of process 180 may include steps 146, 150, 158, 162, 182, and 184. Steps 146 and 182 may occur after step 139; steps 146 and 150 may occur in order; steps 182 and 184 may occur in order; steps 150, 158, and 184 may precede step 186; and steps 186 and 162 may occur in order. Step 186 may be optional, at least as step 186 relates to the first reusable item. Process 180 may also include one or more of the optional steps 142, 144, 148, 152, 154, 156, 164, 166, and 168 of process 140. The optional steps of process 140 may involve the first recoverable item and/or the first reusable item.

Step 184 may include receiving, cleaning, disinfecting, sterilizing, inspecting, testing, marking, refurbishing, recycling, or stocking the first reusable item. Step 184 may also include steps 152, 154, and/or 156 performed on the first reusable item. However, step 184 may involve a different operation than step 150. For example, the first recoverable item may be recycled at the sub-assembly, component part, or raw material level, while the first reusable item may be refurbished and/or recalibrated. In another example, the first recoverable item may be recycled or discarded without being disinfected or sterilized, while the first reusable item may be disinfected or sterilized to render the first reusable item safe for handling during subsequent processing operations prior to terminal sterilization. The differences between steps 150 and 184 may be due to differences between the first recoverable item and the first reusable item, such as the first recoverable item being a recyclable item and the first reusable item being a reusable item.

Figure 9:
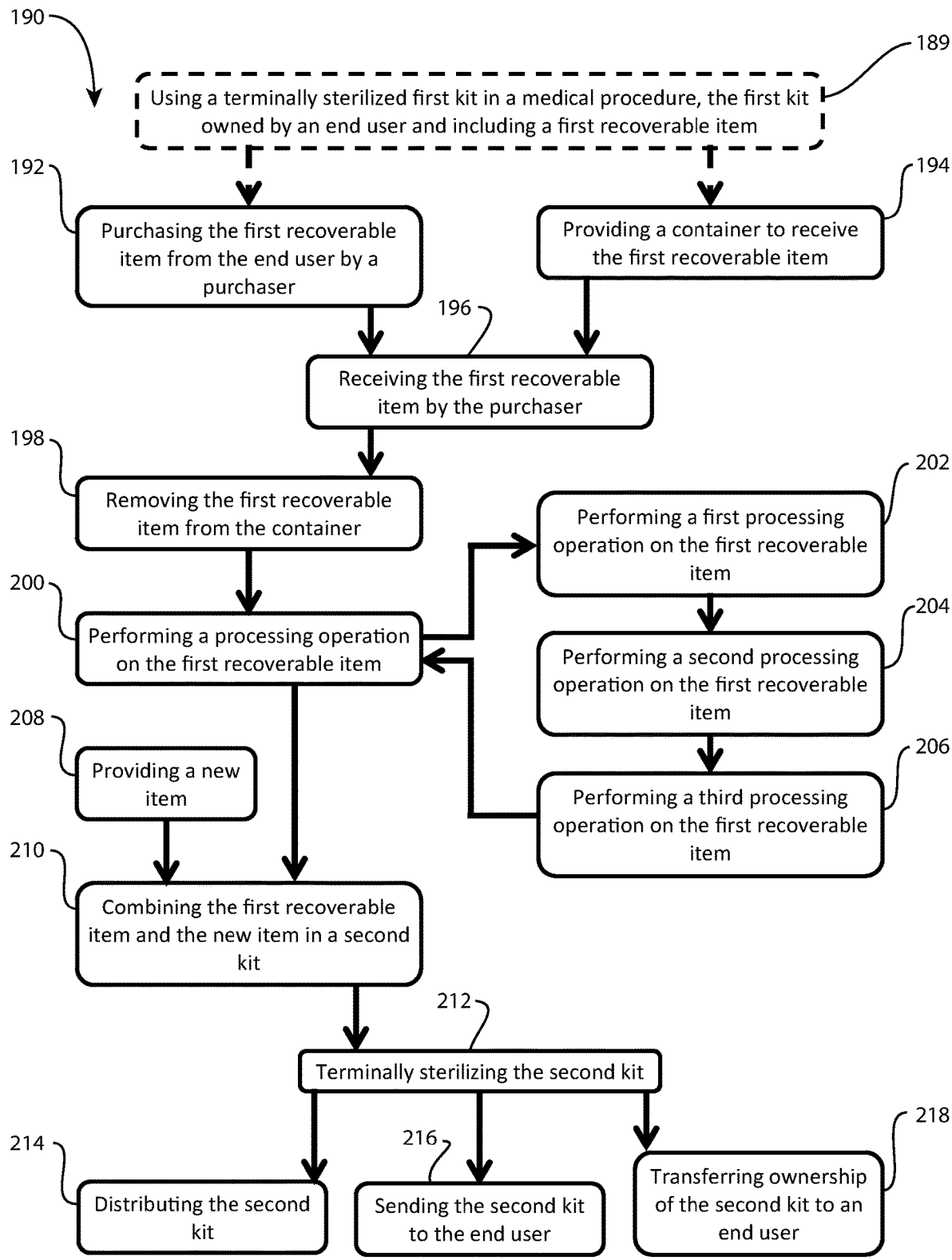
FIG. 9 is a flowchart of yet another process of building a sterile kit.

Referring to FIG. 9, a process 190 may include any or all of the following steps in any order:

Step 192, purchasing a first recoverable item from an owner by a purchaser.

Step 194, providing a container to receive the first recoverable item.

Step 196, receiving the first recoverable item by the purchaser.

Step 198, removing the first recoverable item from the container.

Step 200, performing a processing operation on the first recoverable item.

Step 202, performing a first processing operation on the first recoverable item.

Step 204, performing a second processing operation on the first recoverable item.

Step 206, performing a third processing operation on the first recoverable item.

Step 208, providing a new item.

Step 210, combining the first recoverable item and the new item in a second kit.

Step 212, terminally sterilizing the second kit.

Step 214, distributing the second kit.

Step 216, sending the second kit to the end user.

Step 218, transferring ownership of the second kit to an end user.

FIG. 9 also illustrates a step 189 which may precede the steps 192-218 listed above for process 190. Step 189 is using a terminally sterilized first kit in a medical procedure, the first kit owned by an owner and including the first recoverable item. The owner may be an end user, a facility in which medical procedures are performed, or an original equipment manufacturer (OEM) of the first kit. Step 189 is indicated in dashed lines because this step may occur outside the scope of process 190.

A basic version of process 190 may include steps 192 and 196. Steps 192 and 196 may occur after step 189, and step 192 may precede, occur simultaneously with, or follow step 192. Steps 194, 198, 200, 202, 204, 206, 208, 210, 212, 214, 216, and 218 may be optional steps of process 190.

The purchaser of step 192 may be a processor, a second manufacturer, or the original manufacturer of the first kit.

The first recoverable item of step 192 is a non-consumed item such as a non-selected implant, an instrument, or an accessory for the medical procedure. The first recoverable item may be a reusable item that is included in the second kit after being refurbished. The first recoverable item may be made entirely of materials that are impervious to repeated terminal sterilization cycles. For example, the first recoverable item may be all metal. The first recoverable item may be recovered so that it can be recycled at the sub-assembly, component part, or raw material level. In this situation, the first recoverable item may include some materials that deteriorate when exposed to repeated terminal sterilization cycles. Under certain circumstances, the first recoverable item may be recovered so that it can be discarded.

Step 194 may precede, occur simultaneously with, or follow step 189.

The container of step 194 receives the first recoverable item, protects the first recoverable item from damage during transit, and protects anyone handling the container from exposure to the first recoverable item or other contents of the container. The container may be a package, carton, or box that contained the first recoverable item and/or the first kit. The container may be provided as part of the first kit, independent from any of the packaging of the first kit. The container may be a pouch, bag, envelope, or other item supplied as part of the first kit, sized to hold recoverable items of the first kit. The container may be supplied independently of the first kit, and may be a box, bin, receptacle, drum, or the like that is sized to hold numerous recoverable items from multiple kits. The container may be reusable.

Step 196, receiving the first recoverable item by the purchaser.

Step 198 may occur before step 200. Step 198 may include segregating the first recoverable item from other contents of the container, which may be waste.

Step 200 may include receiving, cleaning, disinfecting, sterilizing, inspecting, testing, marking, refurbishing, disassembling, recycling, stocking, or discarding the first recoverable item. Step 200 may include steps 202, 204, and/or 206.

Step 202 may include cleaning, disinfecting, or sterilizing the first recoverable item. The purpose of this sterilization operation is to render the first recoverable item safe for handling during subsequent processing operations prior to terminal sterilization.

Step 204 may include refurbishing or recycling the first recoverable item. Refurbishing may include sharpening, straightening, calibrating, polishing, passivating, and/or other tasks. Refurbishing may include partial or complete disassembly of the first recoverable item, replacement of at least one component part, and partial or complete reassembly of the first recoverable item.

Step 206 may include inspecting, testing, and marking the first recoverable item. Marking may indicate the number of times the first recoverable item has been refurbished and/or terminally sterilized. Steps 204 and 206 may occur in any order, and process 140 may include multiple instances of steps 204 and/or 206.

The new item of step 208 may be a consumed item or a non-consumed item. The new item may be an implant.

The second kit of step 210 may include a package that contains the first recoverable item and the new item. The package may be a single sterile barrier package or system that contains the first recoverable item and the new item. The package may also be a box or carton that contains one or more sterile barrier packages. The first recoverable item may be contained in a first sterile barrier package and the new item may be contained in a second sterile barrier package. The first and second sterile barrier packages may both be contained in a box, carton, or other outer package.

Step 212 may include gas sterilization, ethylene oxide sterilization, radiation sterilization, ionizing radiation sterilization, gamma sterilization, e-beam sterilization, or liquid chemical sterilization. Step 212 does not include steam sterilization.

Step 214 may involve sending the second kit to a distributor.

Step 216 may involve sending the second kit directly to an end user or a facility in which medical procedures are performed.

Step 218 may involve selling the second kit to the end user or the facility.

Figure 10:
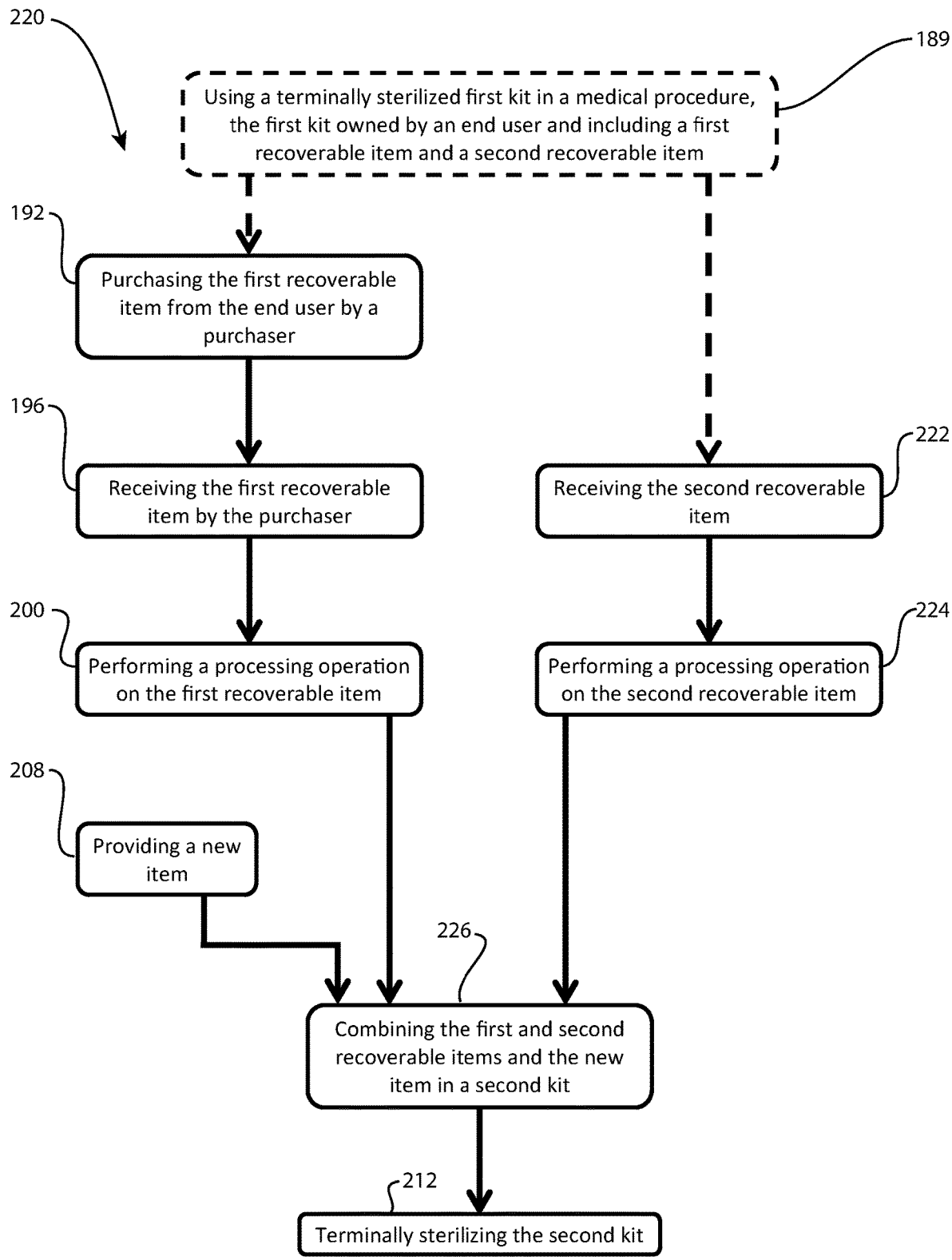
FIG. 10 is a flowchart of a variation of the process of FIG. 9, including a second recoverable item.

Referring to FIG. 10, a process 220 is a variation of process 190 in which a second recoverable item is recovered from the first kit in addition to the first recoverable item. Process 220 may include any or all of the following steps, in any order, in addition to at least the basic steps 192 and 196 of process 190:

Step 222, receiving the second recoverable item.

Step 224, performing a processing operation on the second recoverable item.

Step 226, combining the first recoverable item, the second recoverable item, and the new item in a second kit.

A basic version of process 220 may include steps 192, 196, 222, and 224. Process 220 may also include one or more of the optional steps 194, 198, 200, 202, 204, 206, 208, 210, 212, 214, 216, and 218 of process 190. The optional steps of process 190 may involve the first recoverable item and/or the second recoverable item. Steps 192 and 222 may occur after step 189; steps 192 and 196 may occur in order; steps 222 and 224 may occur in order; steps 200, 208, and 224 may precede step 226; and steps 226 and 212 may occur in order. Step 226 may be optional, at least as step 226 relates to the second recoverable item.

Step 224 may include receiving, cleaning, disinfecting, sterilizing, inspecting, testing, marking, refurbishing, disassembling, recycling, stocking, or discarding the second recoverable item. Step 224 may also include steps 202, 204, and/or 206 performed on the second recoverable item. However, step 224 may involve a different operation than step 200. For example, the first recoverable item may be refurbished, while the second recoverable item may be recycled at the sub-assembly, component part, or raw material level. In another example, the first recoverable item may be disinfected or sterilized to render the first recoverable item safe for handling during subsequent processing operations prior to terminal sterilization, while the second recoverable item may be recycled or discarded without being disinfected or sterilized. The differences between steps 200 and 224 may be due to differences between the first recoverable item and the second recoverable item, such as the first recoverable item being a reusable item and the second recoverable item being a recyclable item. However, in some situations, neither the first nor the second recoverable item is reusable, and the differences between steps 200 and 224 may be due to differences in the design or materials of the first versus the second recoverable item.

Figure 11:
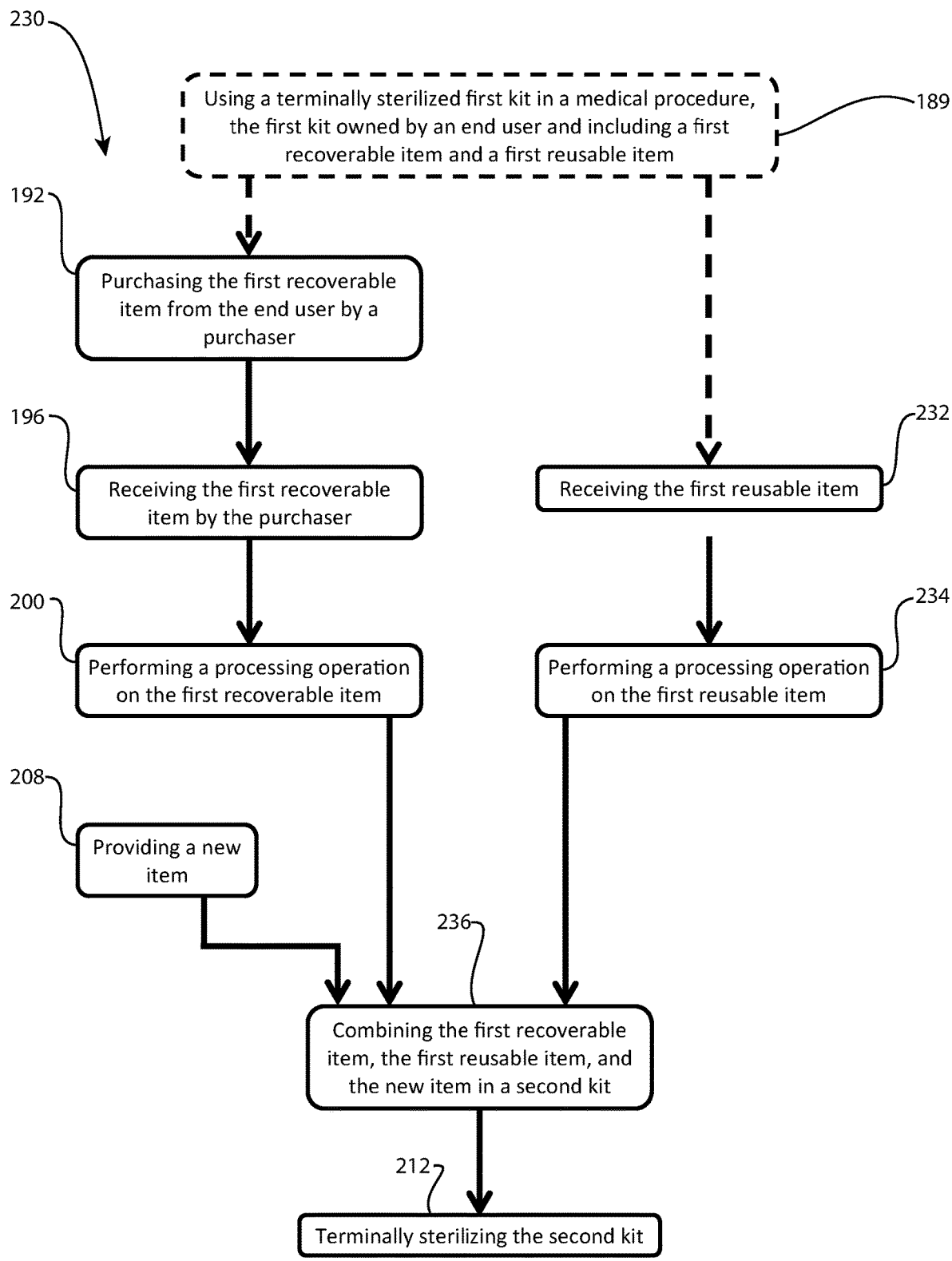
FIG. 11 is a flowchart of another variation of the process of FIG. 9, including a first reusable item.

Referring to FIG. 11, a process 230 is a variation of process 190 in which a first reusable item is recovered from the first kit in addition to the first recoverable item. Process 230 may include any or all of the following steps, in any order, in addition to at least the basic steps 192 and 196 of process 190:

Step 232, receiving the first reusable item.

Step 234, performing a processing operation on the first reusable item.

Step 236, combining the first recoverable item, the first reusable item, and the new item in a second kit.

A basic version of process 230 may include steps 192, 196, 232, and 234. Process 230 may also include one or more of the optional steps 194, 198, 200, 202, 204, 206, 208, 210, 212, 214, 216, and 218 of process 190. The optional steps of process 190 may involve the first recoverable item and/or the first reusable item. Steps 192 and 232 may occur after step 189; steps 192 and 196 may occur in order; steps 232 and 234 may occur in order; steps 200, 208, and 234 may precede step 236; and steps 236 and 212 may occur in order. Step 236 may be optional, at least as step 236 relates to the first reusable item.

Step 234 may include receiving, cleaning, disinfecting, sterilizing, inspecting, testing, marking, refurbishing, recycling, or stocking the first reusable item. Step 234 may also include steps 202, 204, and/or 206 performed on the first reusable item. However, step 234 may involve a different operation than step 200. For example, the first recoverable item may be recycled at the sub-assembly, component part, or raw material level, while the first reusable item may be refurbished and/or recalibrated. In another example, the first recoverable item may be recycled or discarded without being disinfected or sterilized, while the first reusable item may be disinfected or sterilized to render the first reusable item safe for handling during subsequent processing operations prior to terminal sterilization. The differences between steps 200 and 234 may be due to differences between the first recoverable item and the first reusable item, such as the first recoverable item being a recyclable item and the first reusable item being a reusable item.

Figure 12:
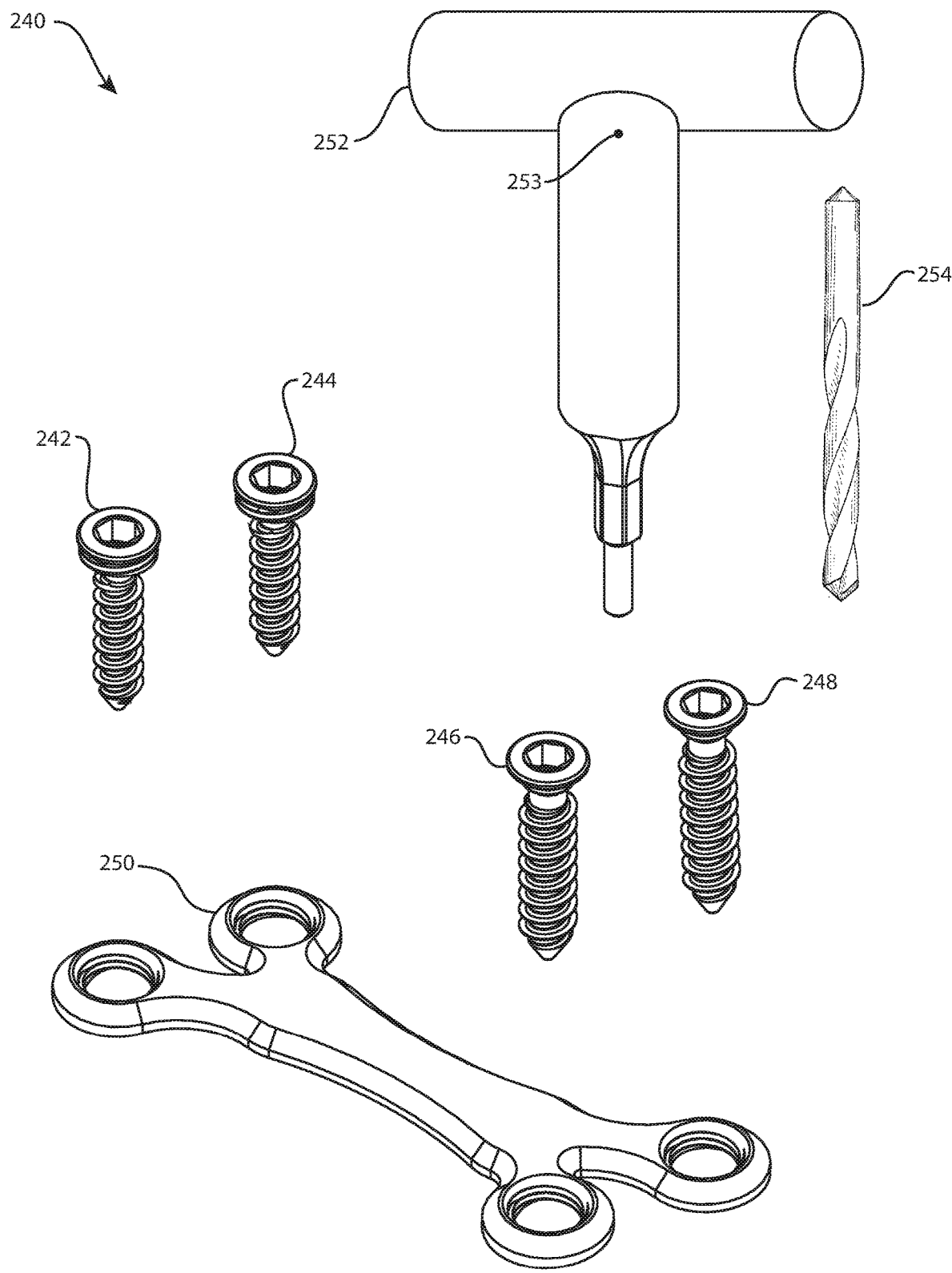
FIG. 12 is a perspective view of items for inclusion in a kit.

Referring to FIG. 12, a kit 240 may include a recovered item 252 and a new item 250. The recovered item may be a reprocessed item or a refurbished item. FIG. 12 illustrates a recovered item 252 that is a medical instrument, namely a screwdriver 252, and a new item 250 that is a medical implant, namely a bone plate 250. The recovered item 252 may bear a mark 253 indicating how many times the recovered item has been recovered or terminally sterilized. The mark 253 may be subtle, such as the dot shown, or more obvious, such as an alphanumeric code or phrase. FIG. 12 illustrates other items, including bone screws 242, 244, 246, 248 and drill bit 254. The bone screws and drill bit may be recovered items or new items.

Figure 13:
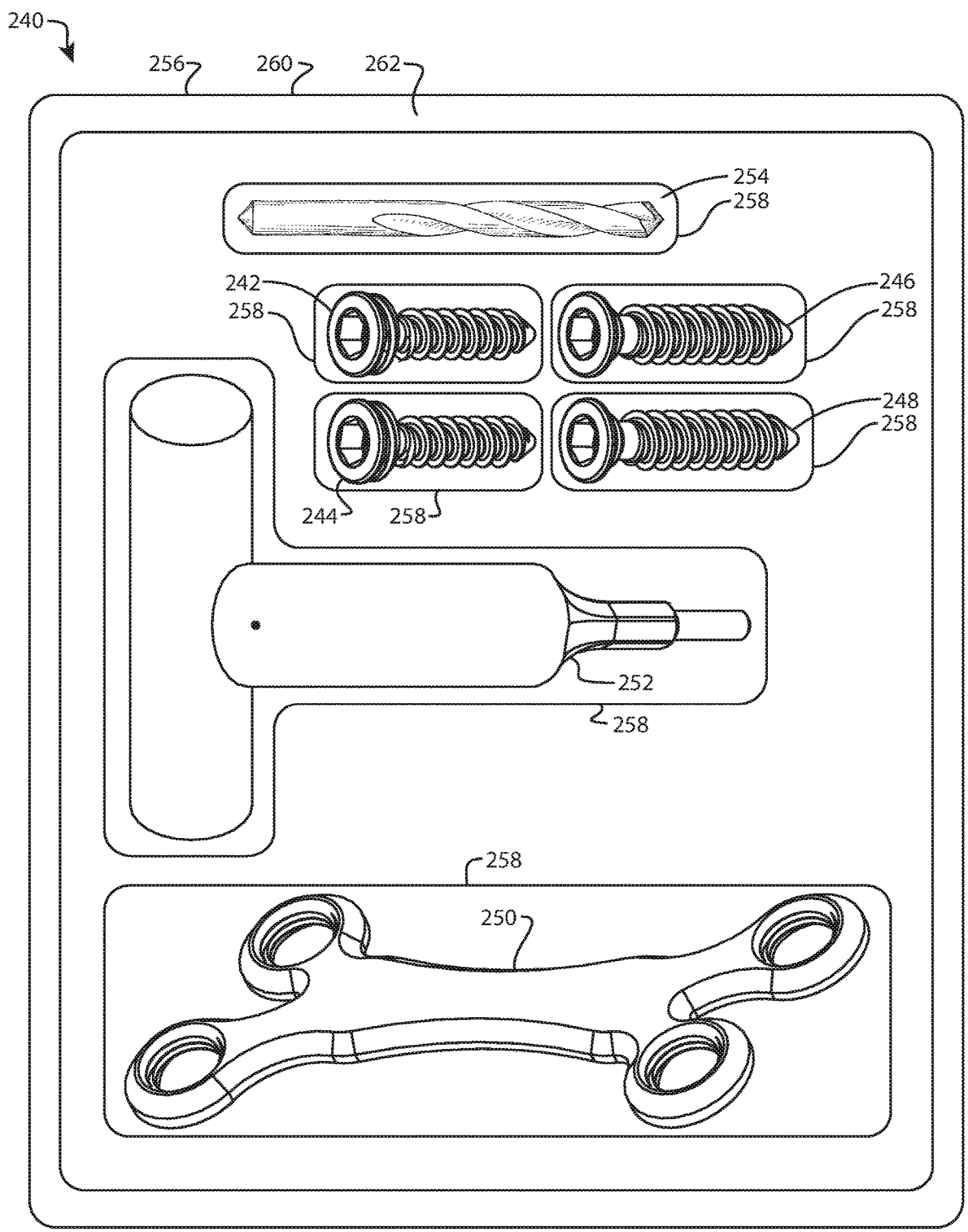
FIG. 13 is a top view of the items of FIG. 12 in a compartmentalized tray of a sterile barrier system.

Referring to FIG. 13, the kit 240 may also include one or more packaging trays 256 which protect the recovered item 252 and the new item 250 and may form part of a sterile barrier package that contains the recovered item 252 and the new item 250. The illustrated packaging tray 256 includes an individual well 258 for each item in kit 240. The packaging tray 256 may include a peripheral flange 260 which may include an area 262 designated for bonding the periphery of the tray 256 to a sheet of lidding stock (not shown), such as non-woven spun bonded polyethylene sheet, to form a sterile barrier package. Alternatively, the tray 256 may be enclosed in one or more nesting pouches (not shown). In FIG. 13, the recovered item 252 and the new item 250 are packaged together and terminally sterilized in a single sterile barrier package as a single stock keeping unit (SKU). Kit 240 may include an outer package, such as a box or carton (not shown).

Figure 14:
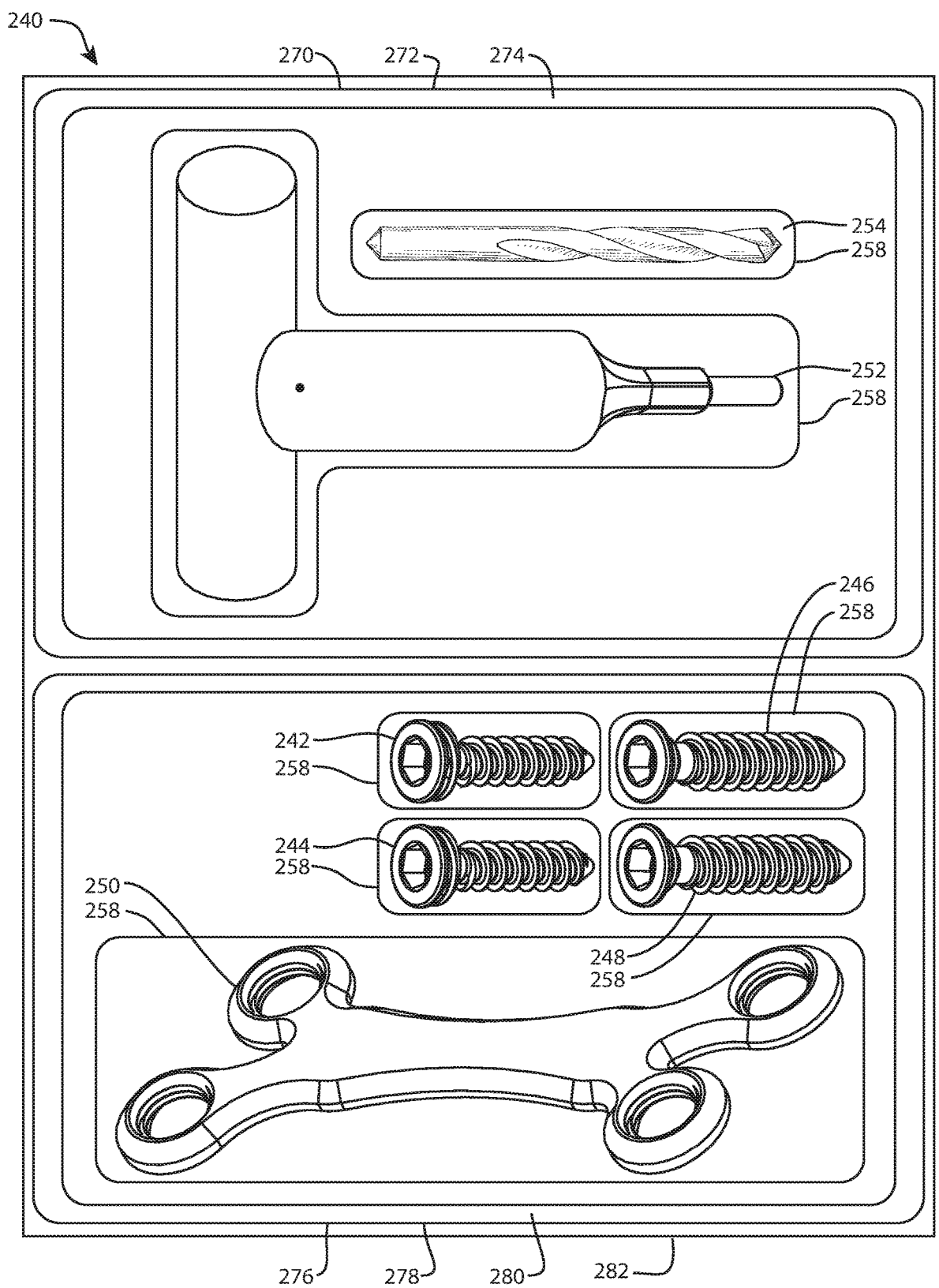
FIG. 14 is a top view of the items of FIG. 12 in compartmentalized trays of sterile barrier systems, all in an outer package.

Referring to FIG. 14, the kit 240 may include two or more packaging trays 270, 276, each tray including an individual well 258 for each item in kit 240. Each tray may include a peripheral flange 272, 278 which may include an area 274, 280 designated for bonding the periphery of each tray 270, 276 to a corresponding sheet of lidding stock (not shown), such as non-woven spun bonded polyethylene sheet, to form a sterile barrier package. Alternatively, the trays 270, 276 may each be enclosed in one or more nesting pouches (not shown). In FIG. 14, the recovered item 252 and the new item 250 are each packaged and terminally sterilized in their own single sterile barrier package. The recovered item 252 is in tray 270 and the new item 250 is in tray 276. The kit 240 also includes an outer package 282 which contains the separate sterile barrier packages and presents kit 240 as a single stock keeping unit (SKU). Outer package 282 may be a box or carton.

The kit 240 may include a container to receive the recovered item after the kit is used. The container may be outer package 282, one of the sterile barrier packages, or a box, bag, pouch, sleeve, or envelope included in the kit 240 outside the sterile barrier package(s). A container may also be supplied separately.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention, as set forth in the claims.

The invention claimed is:

1. A system comprising:
 a recovery container comprising barrier packaging suitable for shipping a biohazard; and
 a kit;
 wherein the kit further comprises:
 at least one first medical device,
   wherein the first medical device is a new medical device having previously not been used in a medical procedure and adapted to engage with an implant or an instrument adapted to engage with a patient's anatomy;
 at least one second medical device,
   wherein the second medical device is a used medical instrument having been previously used in a prior medical procedure and adapted to engage with an implant or an instrument adapted to engage with a patient's anatomy;
   wherein subsequent the prior medical procedure the second medical device is recovered and processed such that it may be used again in another medical procedure, then stored in an inventory location, separate from the first medical device; and
 an outer package further comprising:
   a first tray, wherein the first tray contains a plurality of wells; and wherein the first tray contains the first medical device and the second medical device;
   wherein the first and second medical devices are terminally sterilized after being placed in and sealed within the first tray; and
   wherein the outer package is sealed after the first tray is inserted within the outer package.

2. The kit of claim 1, wherein the outer package further comprises a second tray.

3. The kit of claim 1, wherein the recovery container is adapted to be placed in the outer package with the first tray.

4. The kit of claim 3, wherein the recovery container is a flexible container.

5. The kit of claim 2, wherein one of the first tray or the second tray further comprises a single well and the other of the first tray or the second tray comprises a plurality of wells.

6. The kit of claim 2, wherein the first tray and the second tray contain a plurality of wells.

* * * * *